(12) United States Patent
Sauer

(10) Patent No.: US 12,150,641 B2
(45) Date of Patent: Nov. 26, 2024

(54) SURGICAL ACCESS SYSTEM

(71) Applicant: LSI Solutions, Inc., Victor, NY (US)

(72) Inventor: Jude S. Sauer, Pittsford, NY (US)

(73) Assignee: LSI Solution, Inc., Victor, NY (US)

( * ) Notice: Subject to any disclaimer, the term of this patent is extended or adjusted under 35 U.S.C. 154(b) by 575 days.

(21) Appl. No.: 17/635,461

(22) PCT Filed: Mar. 13, 2020

(86) PCT No.: PCT/US2020/022700
§ 371 (c)(1),
(2) Date: Feb. 15, 2022

(87) PCT Pub. No.: WO2020/186189
PCT Pub. Date: Sep. 17, 2020

(65) Prior Publication Data
US 2022/0313243 A1    Oct. 6, 2022

Related U.S. Application Data

(60) Provisional application No. 62/827,352, filed on Apr. 1, 2019, provisional application No. 62/817,967, filed on Mar. 13, 2019.

(51) Int. Cl.
*A61B 17/34* (2006.01)
*A61B 17/04* (2006.01)
(Continued)

(52) U.S. Cl.
CPC ...... *A61B 17/0469* (2013.01); *A61B 17/3209* (2013.01); *A61B 17/3421* (2013.01);
(Continued)

(58) Field of Classification Search
CPC ............ A61B 17/0469; A61B 17/3209; A61B 17/3421; A61B 17/3496; A61B 90/50;
(Continued)

(56) References Cited

U.S. PATENT DOCUMENTS 3,721,229 A  *  3/1973  Panzer .................. A61M 31/00
606/198
5,591,180 A  *  1/1997  Hinchliffe .......... A61B 17/0469
606/139

(Continued)

FOREIGN PATENT DOCUMENTS

JP     11-503646    3/1999
WO    96/32882     10/1996

OTHER PUBLICATIONS

PCT International Search Report and Written Opinion, mailed May 19, 2020, for International Application No. PCT/US2020/022700, filed Mar. 13, 2020.
(Continued)

*Primary Examiner* — Richard G Louis
(74) *Attorney, Agent, or Firm* — Michael E. Coyne

(57) ABSTRACT

A surgical access system is disclosed. The surgical access system having a cannula may include a distal tip having one or more longitudinal channels distributed around a circumference of the distal tip, and one or more circumferential channels around the distal tip. The surgical access system also includes an obturator coaxially insertable within the cannula which may include a distal tip and a retractable cutting element having an actuator. The surgical access system also includes an articulation interface. The surgical access system may also include a distal tip of the cannula that may further include one or more bridges distributed circumferentially along the one or more circumferential channels of the distal tip. The obturator further may include an elongated tube and a slidable plunger element configured to control fluid flow inside the elongated tube of the obturator.

22 Claims, 26 Drawing Sheets

(51) Int. Cl.
*A61B 17/3209* (2006.01)
*A61B 90/50* (2016.01)
*A61B 17/11* (2006.01)

(52) U.S. Cl.
CPC .......... *A61B 17/3496* (2013.01); *A61B 90/50* (2016.02); *A61B 2017/0472* (2013.01); *A61B 2017/1142* (2013.01); *A61B 2017/3425* (2013.01); *A61B 2017/3488* (2013.01)

(58) Field of Classification Search
CPC .... A61B 2017/0472; A61B 2017/1142; A61B 2017/3425; A61B 2017/3488; A61B 17/3417; A61B 2017/00252
See application file for complete search history.

(56) References Cited

U.S. PATENT DOCUMENTS

| | | | | |
|---|---|---|---|---|
| 5,829,447 | A * | 11/1998 | Stevens | A61F 2/2427 600/374 |
| 6,346,074 | B1 | 2/2002 | Roth | |
| 6,651,672 | B2 | 11/2003 | Roth | |
| 8,852,210 | B2 | 10/2014 | Selover et al. | |
| 2002/0038128 | A1* | 3/2002 | Turovkiy | A61B 17/3417 606/164 |
| 2002/0045908 | A1* | 4/2002 | Nobles | A61B 17/0057 606/144 |
| 2003/0010346 | A1 | 1/2003 | Paolitto et al. | |
| 2004/0087831 | A1* | 5/2004 | Michels | A61B 17/3415 600/114 |
| 2004/0116897 | A1 | 6/2004 | Aboul-Hosn | |
| 2007/0078302 | A1 | 4/2007 | Ortiz et al. | |
| 2007/0203517 | A1 | 8/2007 | Williams et al. | |
| 2013/0085342 | A1* | 4/2013 | Stefanchik | A61B 17/3417 600/232 |
| 2013/0144311 | A1* | 6/2013 | Fung | A61B 17/12013 606/139 |
| 2013/0267938 | A1* | 10/2013 | Greenberg | A61B 18/1477 606/15 |
| 2015/0133958 | A1* | 5/2015 | Singh | A61B 90/10 606/130 |
| 2017/0258466 | A1 | 9/2017 | Prior et al. | |

OTHER PUBLICATIONS

Supplementary Partial EP Search Report, mailed Sep. 15, 2022, EP Application No. 20769764, filed Aug. 17, 2021.

\* cited by examiner

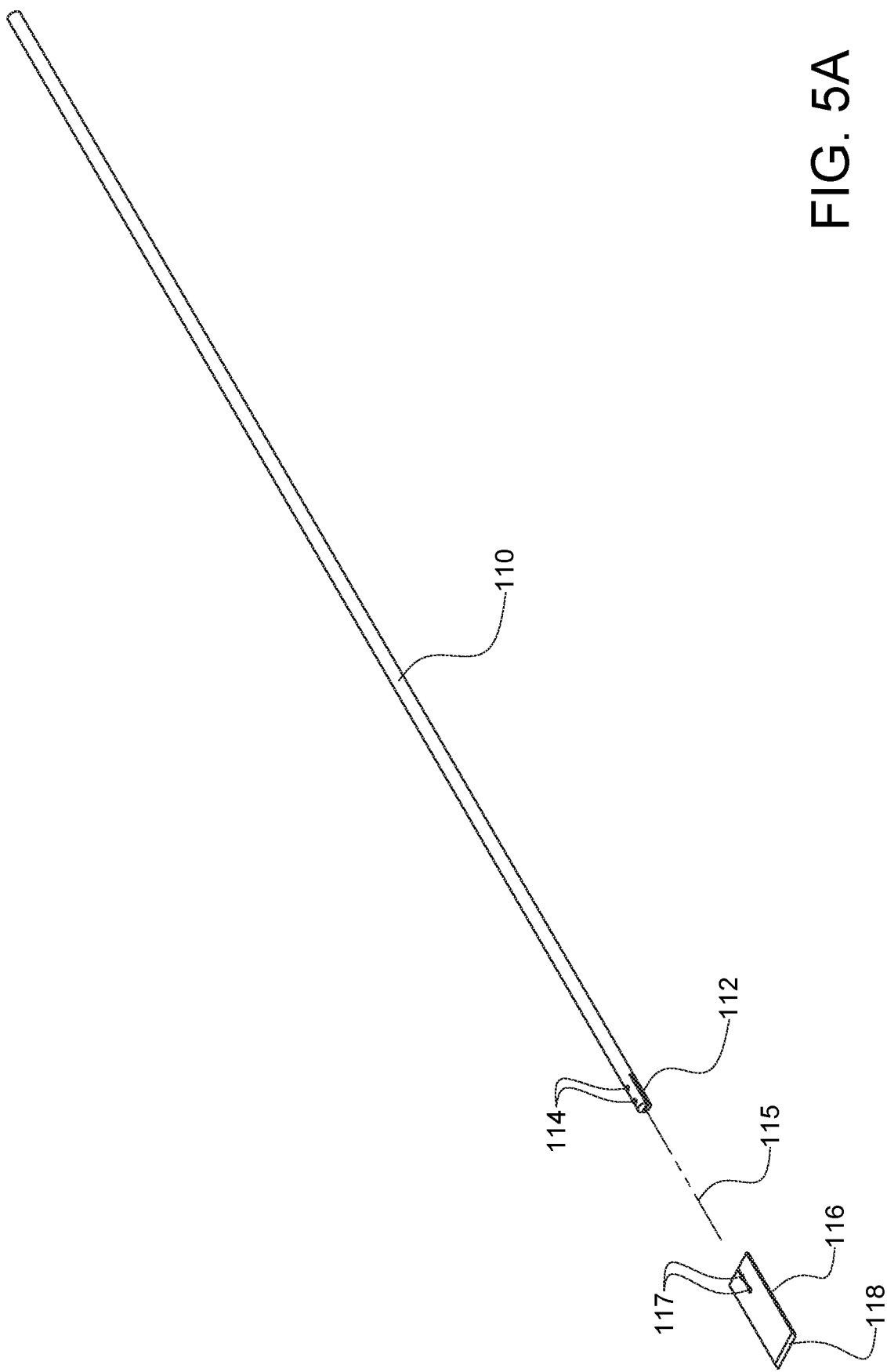

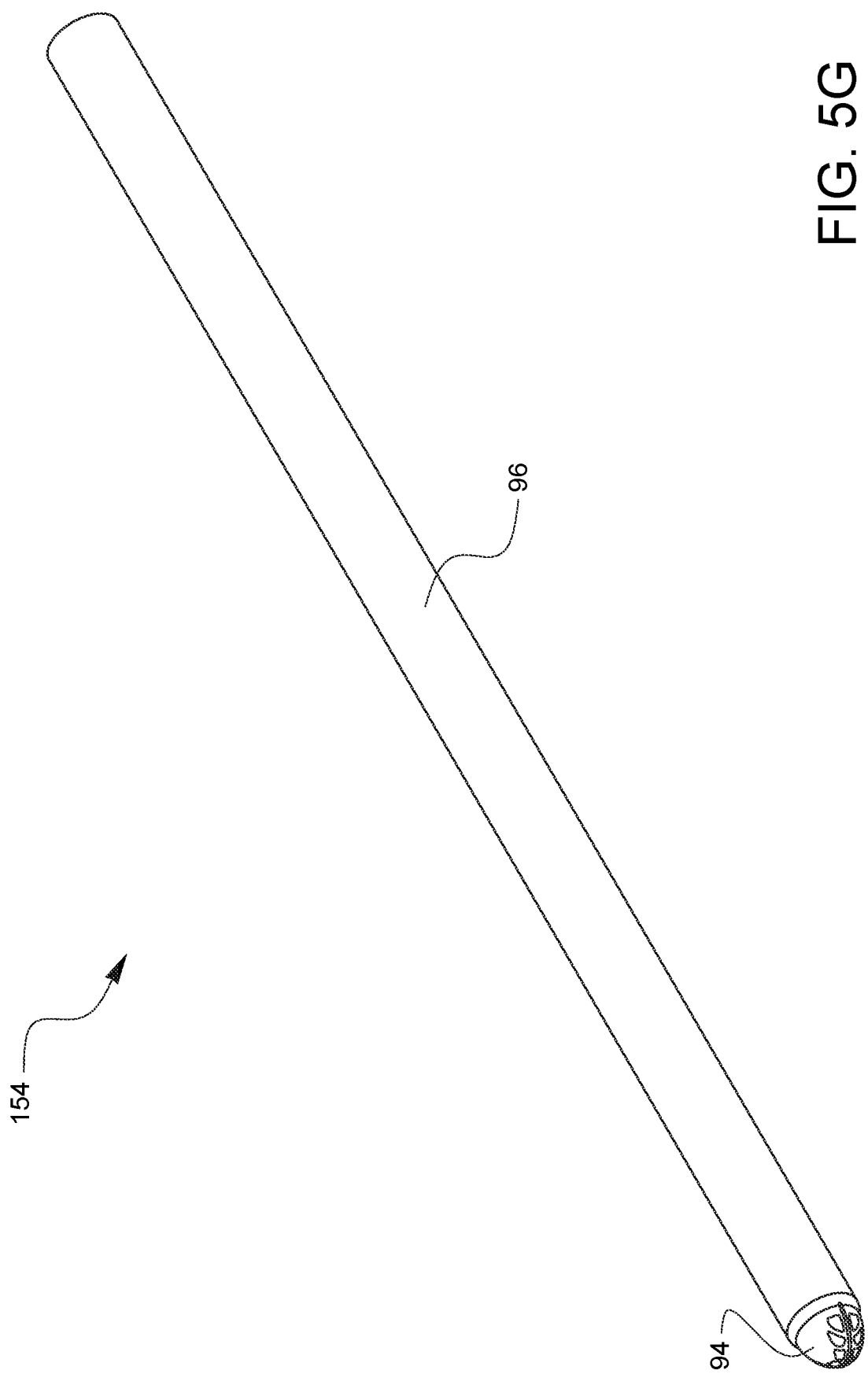

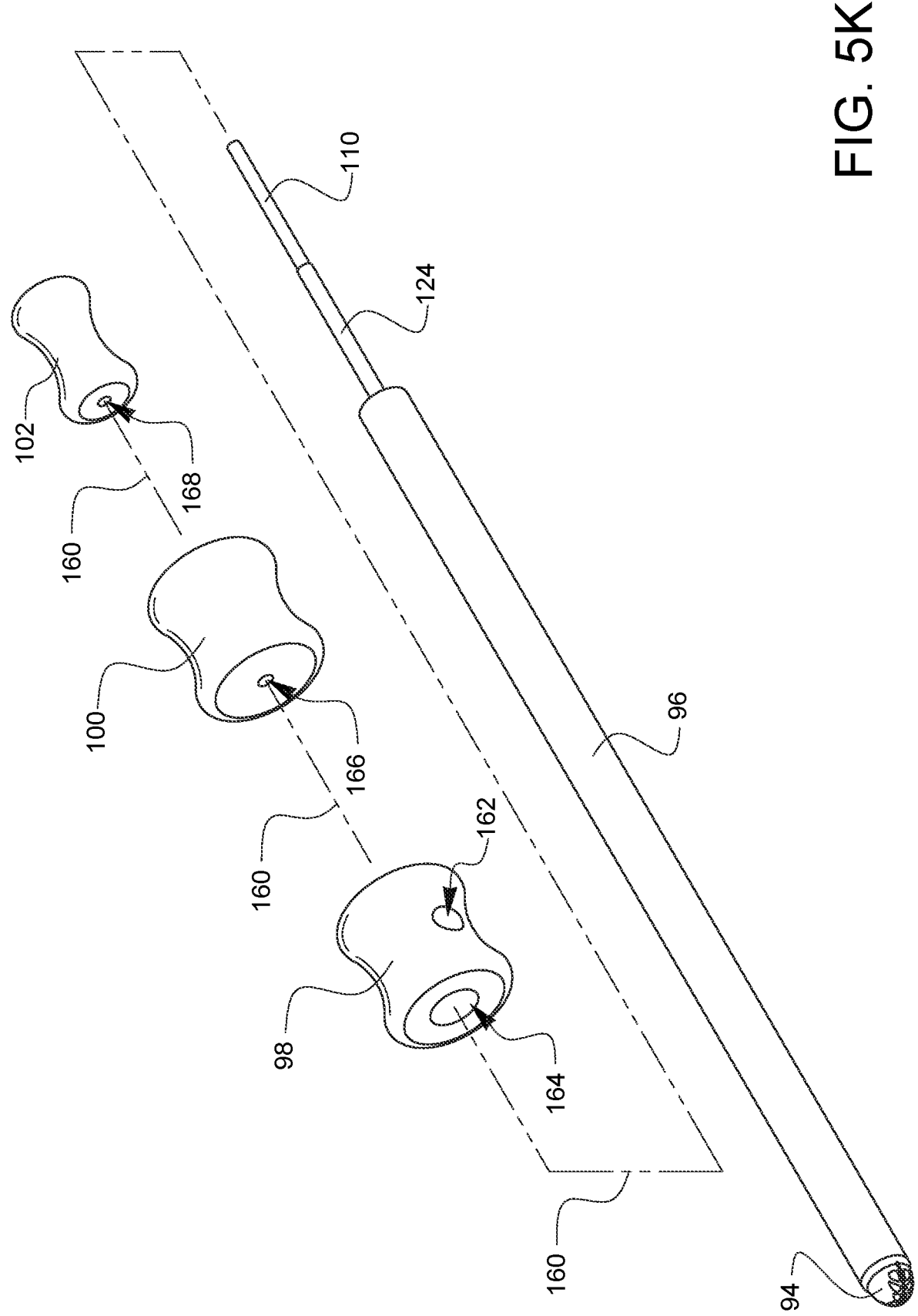

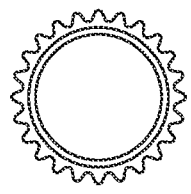
FIG. 8D
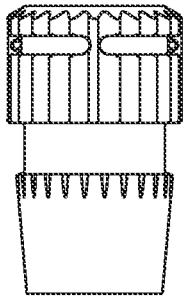
FIG. 8C
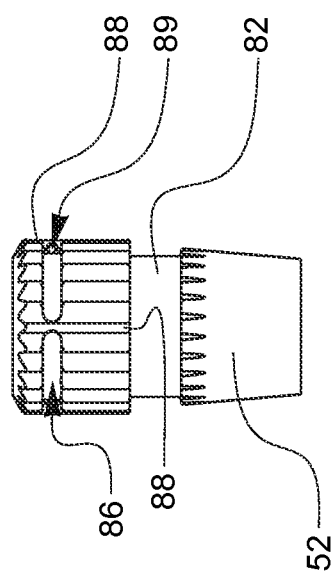 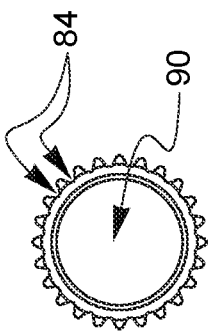 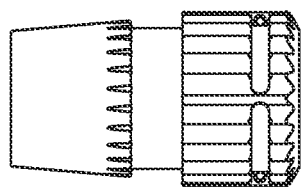
FIG. 8E  FIG. 8A  FIG. 8F
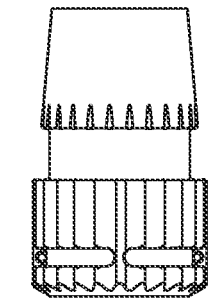
FIG. 8B

SURGICAL ACCESS SYSTEM

RELATED APPLICATIONS

This application is a national stage application, filed under 35 U.S.C. § 371, of International Patent Application No. PCT/US20/22700, filed on Mar. 13, 2020, which claims priority to U.S. Provisional Patent Application No. 62/817,967 filed Mar. 13, 2019, and U.S. Provisional Patent Application No. 62/827,352 filed Apr. 1, 2019, the contents of each of which is incorporated by reference herein in its entirety.

FIELD

The claimed invention relates to surgical devices, and more specifically to a surgical access device or system useful in the correction of tricuspid regurgitation and methods thereof.

BACKGROUND

The availability of safe and effective therapy for tricuspid valve (TV) disease remains an area of significant unmet clinical need. Tricuspid regurgitation (TR) or the pathologic leakage of blood back into the right atrium during systole, quite common in cardiac patients with left-sided valvular or myocardial disease, is estimated to affect >1.5 million people in the United States, with a yearly incidence of about 200,000 and >300,000 patients in the United States and Europe, respectively. Specific anatomic features from the TV complex might vary according to the causing mechanism (primary vs. secondary) and throughout the progressive stages of ventricular remodeling in patients with functional TR. TR is most often functional, primarily due to annular dilatation and leaflet tethering from right ventricular remodeling caused by left-sided heart disease, atrial fibrillation, or pulmonary hypertension. Primary TR accounts for ~10% of cases of TR and can be due to congenital (Ebstein's anomaly, prolapse) or acquired diseases (rheumatic, endocarditis, carcinoid, endomyocardial fibrosis, intracardiac leads, or bioptome-related iatrogenic trauma). Today, TV disease is often considered a marker for late-stage chronic heart failure. TV is associated with a grim prognosis with most patients receiving lifetime medical therapy until intractable right heart failure and end-organ dysfunction appear.

Secondary TR has been divided into three stages for therapeutic purposes. In the early stage, initial dilation of the right ventricle leads to tricuspid annular dilation without significant leaflet tethering. Annular-based systems should easily repair TR in these first stages. In the absence of long-term durability data for transcatheter TV therapy and on the basis of a surgical predicate, ring may be preferred over suture annuloplasty when possible in order to reduce TR recurrence. In the second stage, progressive right ventricular and tricuspid annular dilation develop, impairing leaflet coaptation. The likelihood for successful Transcatheter Tricuspid Valve Repair (TTVr) using annuloplasty alone is less suitable in cases with progressive tethering and tricuspid annular dilation. Finally, as the right ventricle continues to remodel, further leaflet tethering worsens, resulting in a lack of coaptation and massive or torrential TR. When severe tethering occurs, any repair attempt could be considered futile.

FIG. 1A is a side cross-sectional view of a heart. The heart 10 is shown schematically with some of the relevant anatomical features in view. The tricuspid valve 16 (TV) is a complex structure, with several anatomic peculiarities rendering it unique. The TV apparatus, shown in FIG. 1A, normally has three leaflets, the septal leaflet 22, the posterior leaflet 24, and the anterior leaflet 20, chordae tendineae 26, and usually three papillary muscles 28. Also shown are the general locations of a superior vena cava 12 and an inferior vena cava 14.

As shown in FIG. 1B, the tricuspid annulus valve 16 is the largest of four heart valves, with very thin, fragile leaflets composing a potentially large regurgitant orifice area. The tricuspid valve 16 is surrounded by the tricuspid valve annulus 18 a saddle-shaped ellipsoid that becomes planar and circular as it dilates primarily in the anterolateral free wall in patients with left-sided heart disease with sinus rhythm verses expanding mostly along the posterior border with less prominent leaflet tethering in patients with functional TR secondary to chronic atrial fibrillation. The three leaflets, an anterior leaflet 20, septal leaflet 22, and posterior leaflet 24 are also shown in FIG. 1B. The relative locations of a mitral valve 34 and mitral annulus 36, as well as a aortic valve 30 and aortic annulus 32, and a pulmonary valve 38 and pulmonary annulus 40 are also indicated for reference. Four chief anatomic structures surround the TV and are therefore at risk for interventions addressing TV disease: the conduction system (atrioventricular node and the right bundle of His) coursing the membranous septum at 3 to 5 mm from the anteroseptal commissure, the right coronary artery (encircling the right atrioventricular groove—5.5 mm from the septal and posterior portions, 7 mm from the anterior portion), the non-coronary sinus of Valsalva, and the coronary sinus ostium being an important landmark of the posteroseptal commissure. The TV apparatus poses additional challenging issues to overcome: lack of calcium, angulation in relation to the superior vena cava (SVC) and inferior vena cava (IVC), a trabeculated and thin right ventricle hindering a transapical approach, or the presence of pre-existing cardiac implantable electronic devices.

Traditional isolated TV surgery typically requires highly invasive surgical access and cardio-pulmonary by-pass. Since this current approach continues to be associated with one of the highest risks of mortality among all cardiac valve procedures in contemporary practice (operative mortality rates of 8.8% to 9.7%), it is rarely utilized relative to the large number of untreated TR patients (only 5,005 isolated tricuspid procedures were performed in a large contemporary U.S. nationwide registry over a 10-year period). Durability remains the Achilles heel of most surgical interventions addressing the TV. Many factors, such as right ventricular remodeling and dysfunction, tricuspid annular size progression, and pulmonary hypertension, may contribute to the high rates of TR recurrence observed following surgical TR correction. Surgical experience has shown more sustained durability of ring annuloplasty compared with suture annuloplasty, as well as for TV replacement over repair. However, concerns about increased perioperative mortality for TV replacement compared with repair in contemporary series—somewhat linked to selection bias of patients with larger tricuspid annular dilation and more severe right ventricular dysfunction—have led to a trend over time toward TV repair rather than replacement.

Modern advances in cardiac surgery have made it possible to repair or replace heart valves using minimally invasive surgical techniques. As minimally invasive techniques have improved, surgeons have been able to operate on patients through smaller and smaller access holes, resulting in less perioperative pain and shorter recovery times. While more steps continue to be taken to reduce the amount of time a patient must be on cardio-pulmonary bypass (CPB), surgeons continue to push the boundaries of what is possible by striving to be able to perform certain surgeries on a beating heart without the need for CPB. It would be even more desirable to be able to perform specific cardiac surgical procedures on a beating heart under minimally invasive conditions. For example, it would be highly desirable to be able to perform a tricuspid valve repair through a cannula placed between a patient's ribs and into the right atrium of the heart while the heart is still beating. The pressure in the right atrium is such that the blood would tend to fill partially into such a cannula, and of course, there would be blood within the right atrium which would also, unfortunately, completely obscure a surgeon's view of the right atrium and the tissues of the tricuspid valve if such an approach were to be taken. Even echocardiography, on its own, would have a difficult time allowing the surgeon to orient a suturing device through the blood field for a series of related stitches. Therefore, it would be desirable to have a minimally invasive suture placement system and method which would provide access to and enable reliable suture placement around a cardiac valve, such as a tricuspid valve, even under conditions of zero direct and zero endoscopic visibility to enable minimally invasive beating heart surgery for better patient outcomes. Faster and more reliable cardiac operations offer additional benefits, such as reduced surgical team fatigue and more efficient use of critical resources. Expediting cardiac surgery can also improve patient outcomes. Minimally invasive surgical access systems could find utility in other areas of surgery or surgical procedures.

SUMMARY

A surgical access system is disclosed. The surgical access system having a cannula may include a distal tip having one or more longitudinal channels distributed around a circumference of the distal tip, and one or more circumferential channels around the distal tip. The surgical access system also includes an obturator coaxially insertable within the cannula which may include a distal tip and a retractable cutting element having an actuator. The surgical access system also includes an articulation interface.

The surgical access system may also include a distal tip of the cannula that may further include one or more bridges distributed circumferentially along the one or more circumferential channels. The obturator further may include an elongated tube. The obturator further may include a slidable plunger element configured to control fluid flow inside the elongated tube of the obturator.

A method of accessing a surgical site is also disclosed. The method of accessing a surgical site also includes placing at least one pursestring suture in a wall of a heart, securing the at least one pursestring suture to a cannula, placing an obturator tip of a surgical access system having a retractable blade in contact with the wall of a heart, incising the wall with the retractable blade, and securing the incised wall to the cannula of a surgical access system.

BRIEF DESCRIPTION OF THE DRAWINGS

FIGS. 8A-8F are front, left side, right side, rear, top, and bottom elevational views, respectively, of the distal tip of the cannula of FIG. 2.

DETAILED DESCRIPTION

Figure 1A:
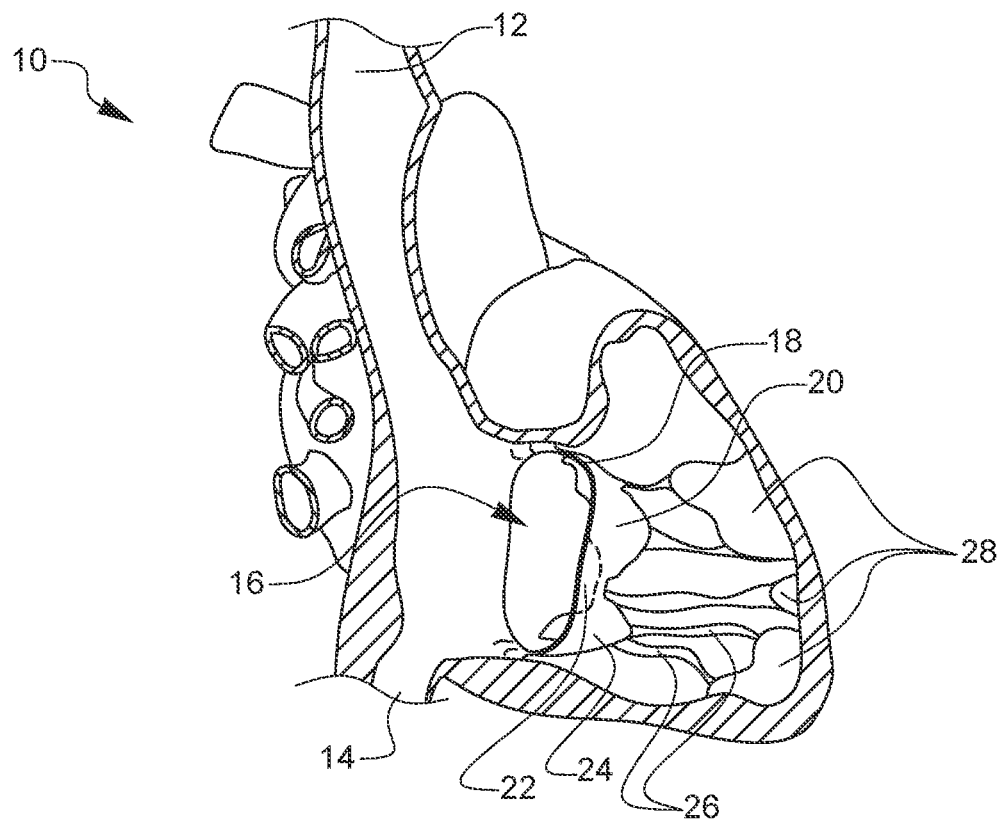
FIGS. 1A-1B are side and top cross-sectional views of a human heart, respectively.
Figure 1B:
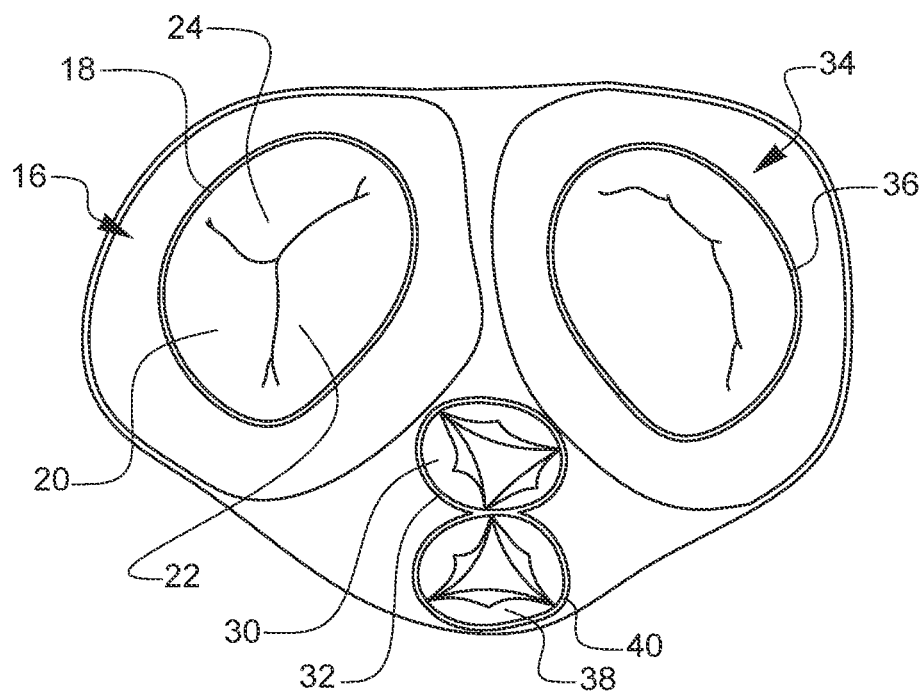
Figure 2:
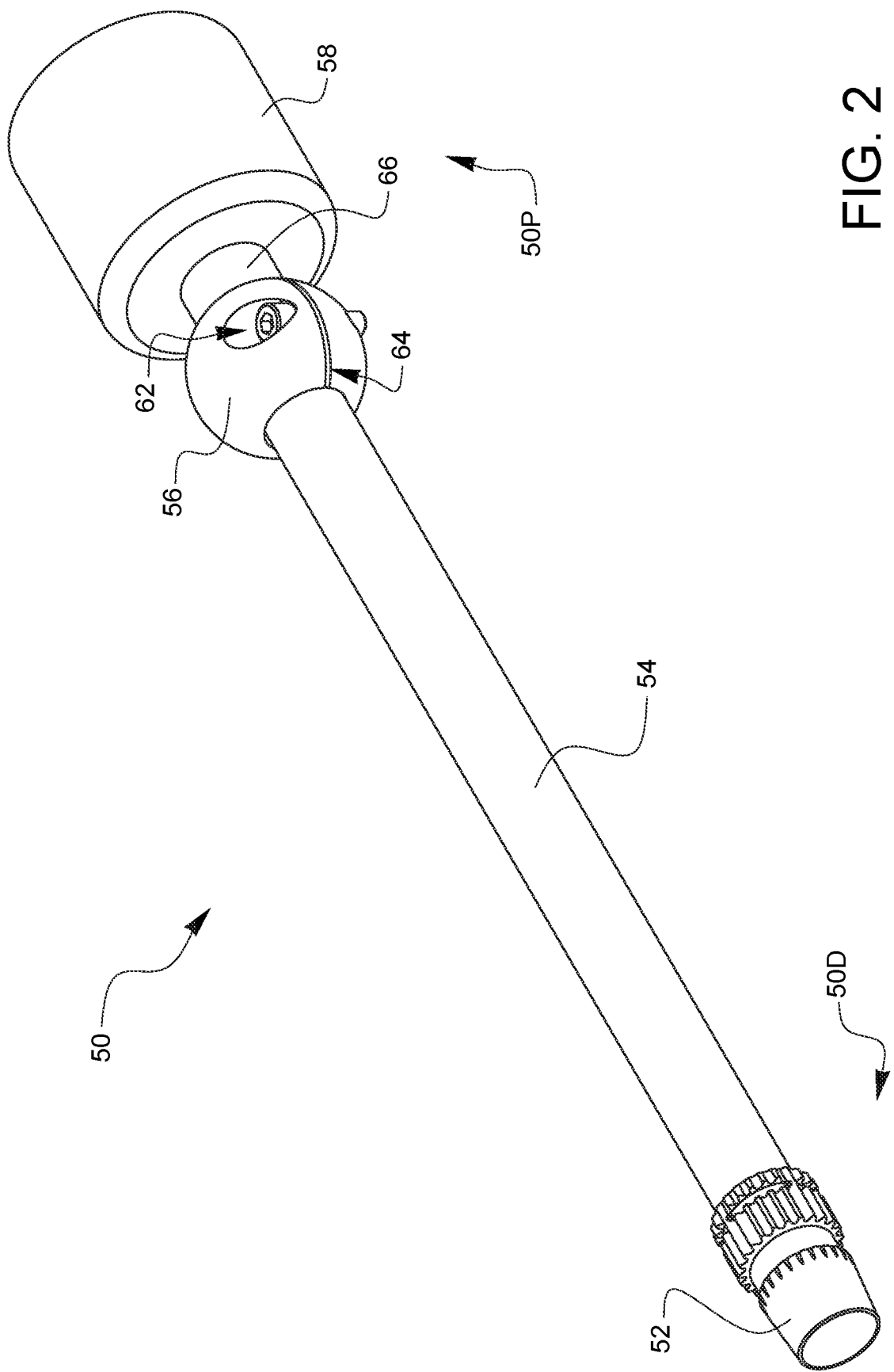
FIG. 2 is a top-right perspective view of a cannula for use in a surgical access system.

FIG. 2 is a top-right perspective view of a cannula for use in a surgical access system. The cannula 50 has a proximal end 50P which is oriented closest to a surgeon and a distal end 50D oriented away from a surgeon during use. The cannula 50 has a cannula top 58 at the proximal end 50P coupled to a cannula top coupler 66 and then coupled to a cannula tube 54. The cannula tube is a hollow elongated tube in this illustrated embodiment. A cannula distal tip 52 is coupled to the distal end 50D of the cannula tube 54. The cannula 50 has a universal ball joint 56 slidably engaged onto the cannula tube 54 of the cannula 50. The universal ball joint 56 defines an opening 64 and a set screw channel 62. The opening 64 is located opposite a hinge (not shown in this view). The universal ball joint 56 is configured such that the universal ball joint 56 may be slidable along the length of the cannula tube 54 and be set at the discretion of the surgeon based on anatomical variations between patients based on the distance between a chest wall and a right atrium of a patient's heart, for example, or for other anatomical distances inherent to a particular surgical site to which one might wish to gain access. Once a desired location for the universal ball joint 56 is determined, a set screw 63 is inserted along axis 65 and tightened to restrict the universal ball joint 56 from moving during a minimally invasive surgical procedure. While a set screw channel 62 is shown in this embodiment, and a tension adjusting set screw 63 is described in regard to this embodiment, other means of setting, adjusting, or readjusting the tension of the universal ball joint 56 or other similar slidable joint may be obvious to one skilled in the art. This universal ball joint 56 may be separate from or continuous with the cannula 50. The universal ball joint 56 or alternate embodiments thereof may be referred to as an articulation interface. An articulation interface for the surgical access system described herein is an interface coupled to or connected to the surgical access system that allows for and is configured to provide repositionable and independent movement in three planes. In an anatomical context these three planes of movement may be referred to as sagittal, frontal, and transverse, while in a Cartesian coordinate system the three planes may be referred to as x, y, and z. It should be understood that these referential planes of movement are provided for context and are intended to cover alternate reference planes or descriptions of planes of movement.

Figure 3:
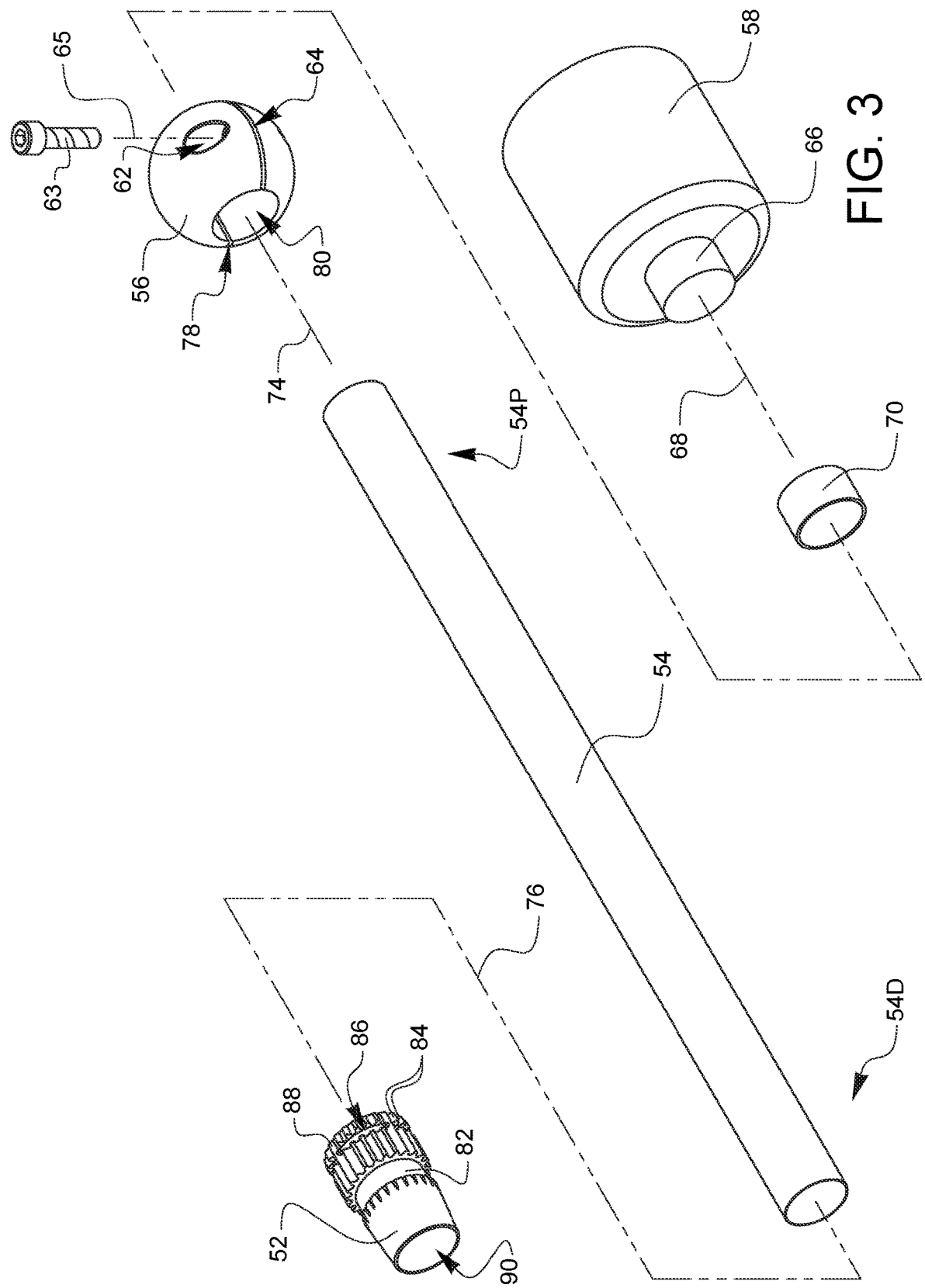
FIG. 3 is an exploded view of the assembly steps for the cannula of FIG. 1.

FIG. 3 is an exploded view of the assembly steps for the cannula of FIG. 2. The cannula distal tip 52 further defines a circumferential pursestring suture channel 82, several longitudinal grooves 84 or longitudinal channels, a cinch suture channel 86, several bridges 88, the bridges 88 further defining a bridge orifice 89 (not shown in this view), and a cannula tip opening 90. The cinch suture channel 86 and the pursestring suture channel 82 are circumferential channels located on the cannula tip 52 and configured to provide an indentation to guide a suture or tissue or other material within that circumferential channel. It should be understood that the term "suture," as used herein, is intended to cover any thread, cable, wire, filament, strand, line, yarn, gut, or similar structure, whether natural and/or synthetic, in monofilament, composite filament, or multifilament form (whether braided, woven, twisted, or otherwise held together), as well as equivalents, substitutions, combinations, and pluralities thereof for such materials and structures.

Additional functions of the various channels and other features of the cannula distal tip 52 will be further described later in regard to FIGS. 7A-7E. The cannula tip 52 is placed onto and fixedly attached to the distal end 54D of the cannula tube 54 along axis 76. The universal ball joint 56 defines the set screw channel 62 and opening 64, and further defines a flexible hinge 78 and a center channel 80. The flexible hinge is configured to allow the universal ball joint 56 to open slightly and allow the universal ball joint 56 to be slidable along the length of the cannula tube 54 when not under tension from a set screw, for example. The universal ball joint 56 is next placed on the proximal end 54P of the cannula tube 54 along axis 74. The universal ball joint 56 may be located at any point along the cannula tube 54 depending on any anatomical variations in distance related to the external position of a patient relative to the internal surgical site being accessed. Finally, the cannula top 58, which defines a cannula top coupler 66 is fixedly coupled over a cannula tube spacer 70 along axis 68, and the cannula top 58 is fixedly attached to the proximal end 54P of the cannula tube 54. This step holds the universal ball joint 56 captive along the length of the cannula tube 54. The components assembled in FIG. 3 are fixedly attached via brazing, welding, ultrasonic welding or by other means of joining known to those skilled in the art. Furthermore, individual components described in relation to the assembly of the cannula may be formed in combination and may not necessarily be separate components.

Figure 4:
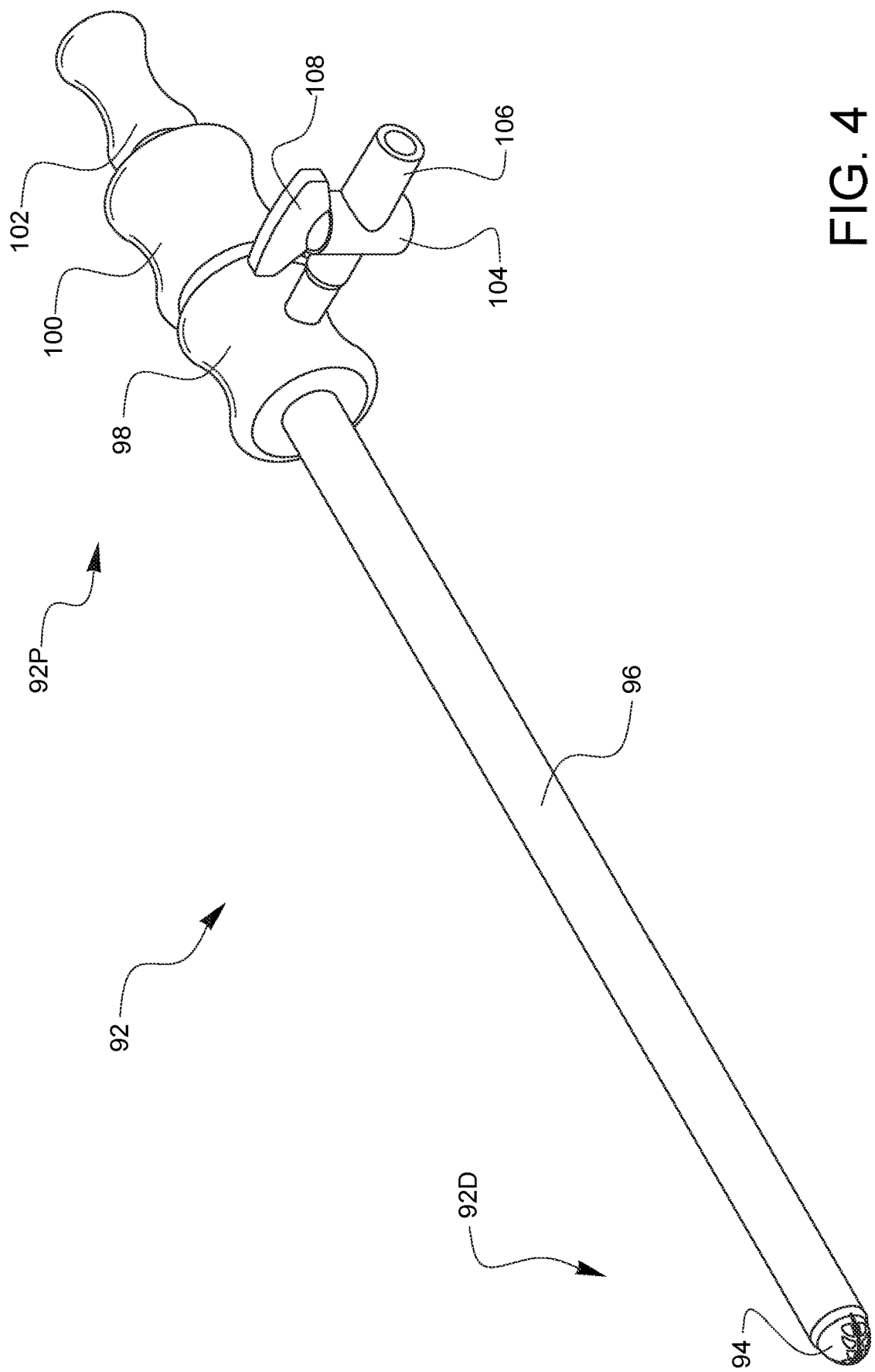
FIG. 4 is perspective view of an obturator for use in a surgical access system.

FIG. 4 is perspective view of an obturator for use in a surgical access system. The obturator 92 has a proximal end 92P which is oriented closest to a surgeon and a distal end 92D oriented away from a surgeon during use. The obturator 92 has an obturator distal tip 94 coupled to an obturator tube 96 at the distal tip 92D of the obturator 92. The specific details and features of this obturator distal tip 94 will be discussed later in regard to FIG. 5F. The proximal end 92P of the obturator 92 has an obturator knob 98, a plunger knob 100, and a cutter knob 102. These knobs 98, 100, 102 can be actuated by the operator to utilize the features of the obturator 92 portion of the surgical access system described herein. The obturator knob 98 further defines a stopcock 104, which further defines a vacuum inlet 106 and a valve 108. The vacuum inlet can be connected to a source for delivering vacuum or other fluid flow to or from the obturator distal tip 94. The magnitude of flow can be controlled, turned on, or turned off by actuating the valve 108. The assembly and specific features and details of the components of the obturator 92 will be discussed in regard to FIGS. 5A-5N. Alternate means of fluid flow or airflow regulation known to one skilled in the arts may also be used.

Figure 5B:
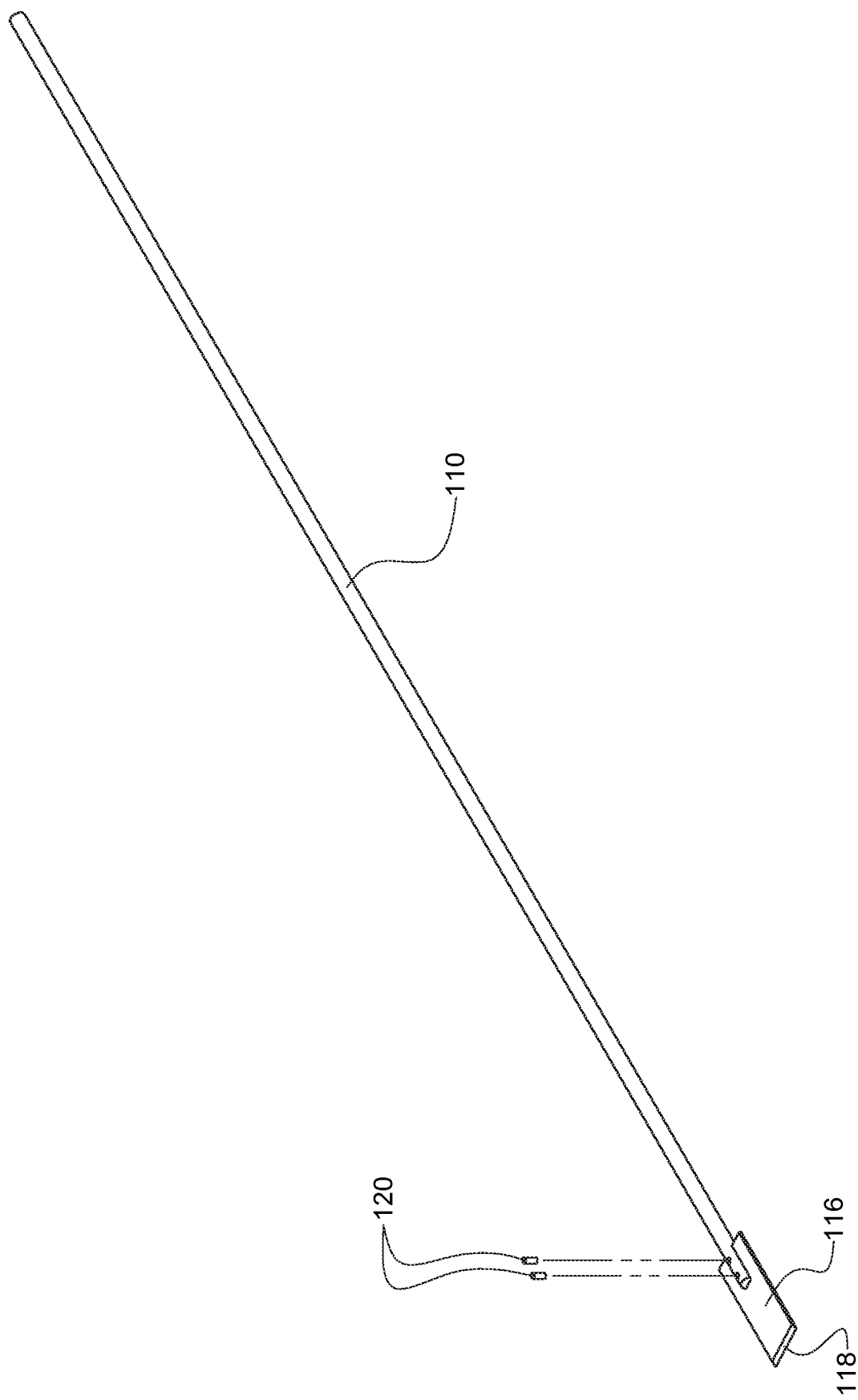
FIG. 5A-5N are a series of exploded and perspective views of assembly steps for the obturator portion of the surgical access system of FIG. 3.
Figure 5C:
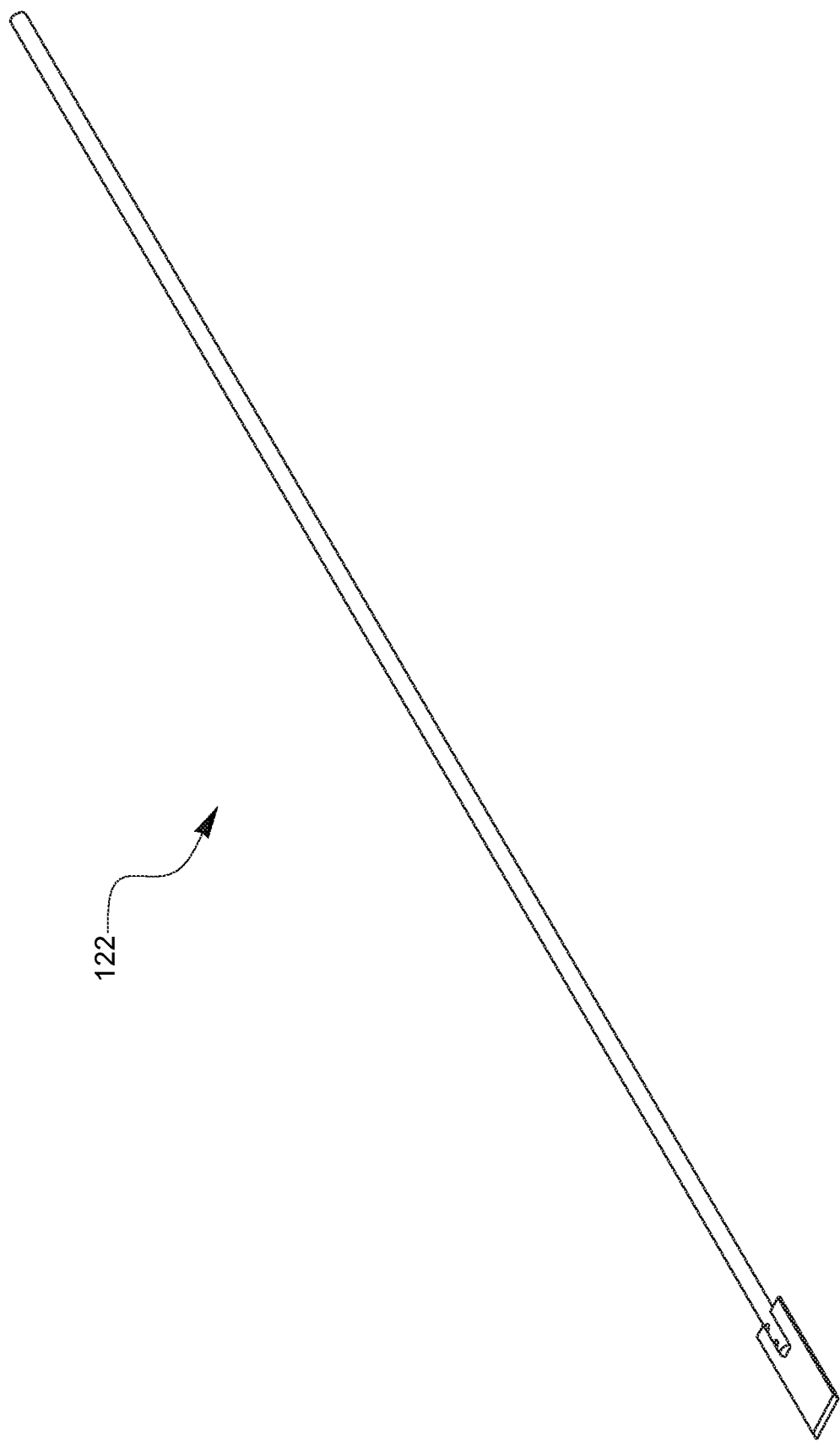
Figure 5D:
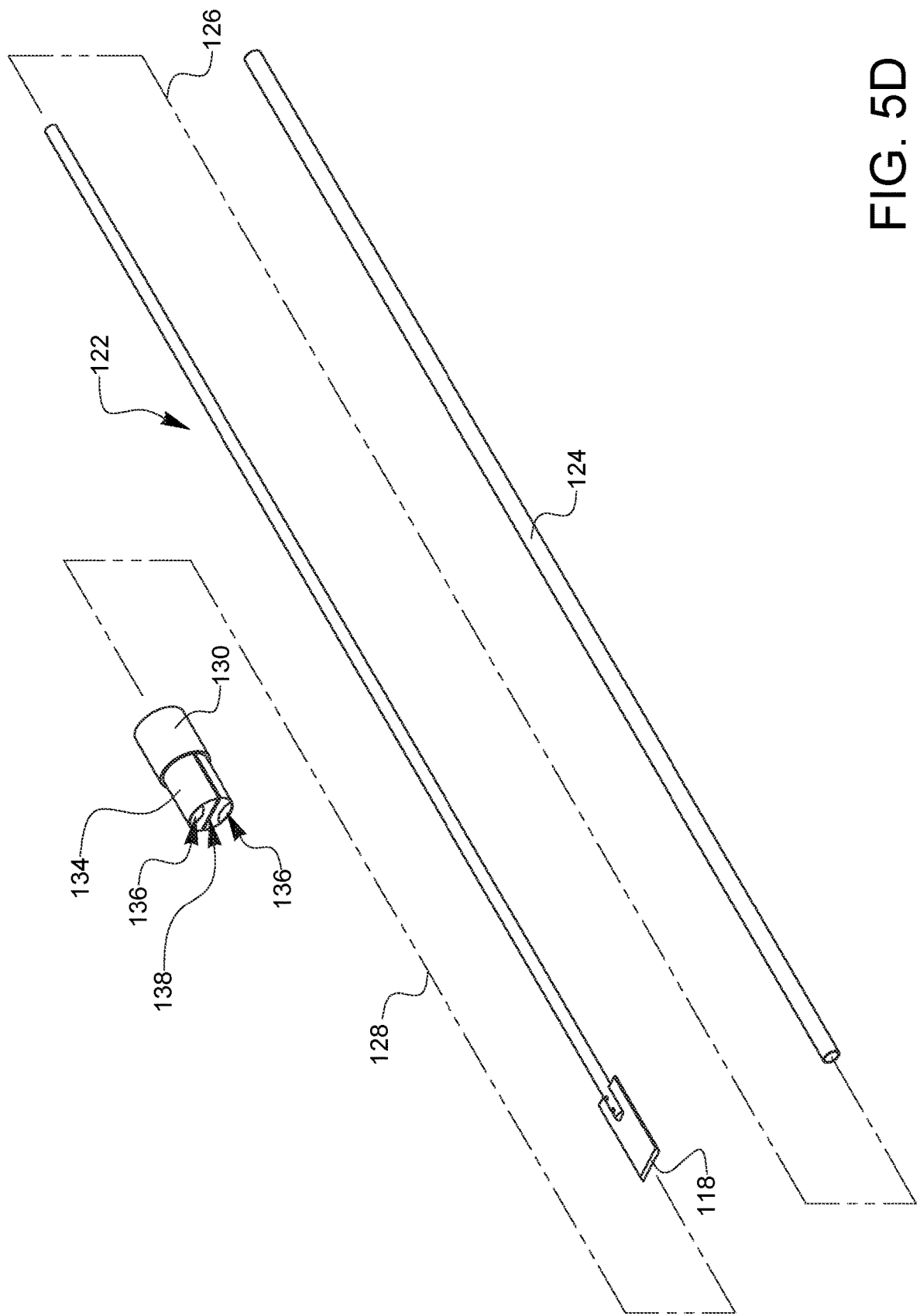
Figure 5E:
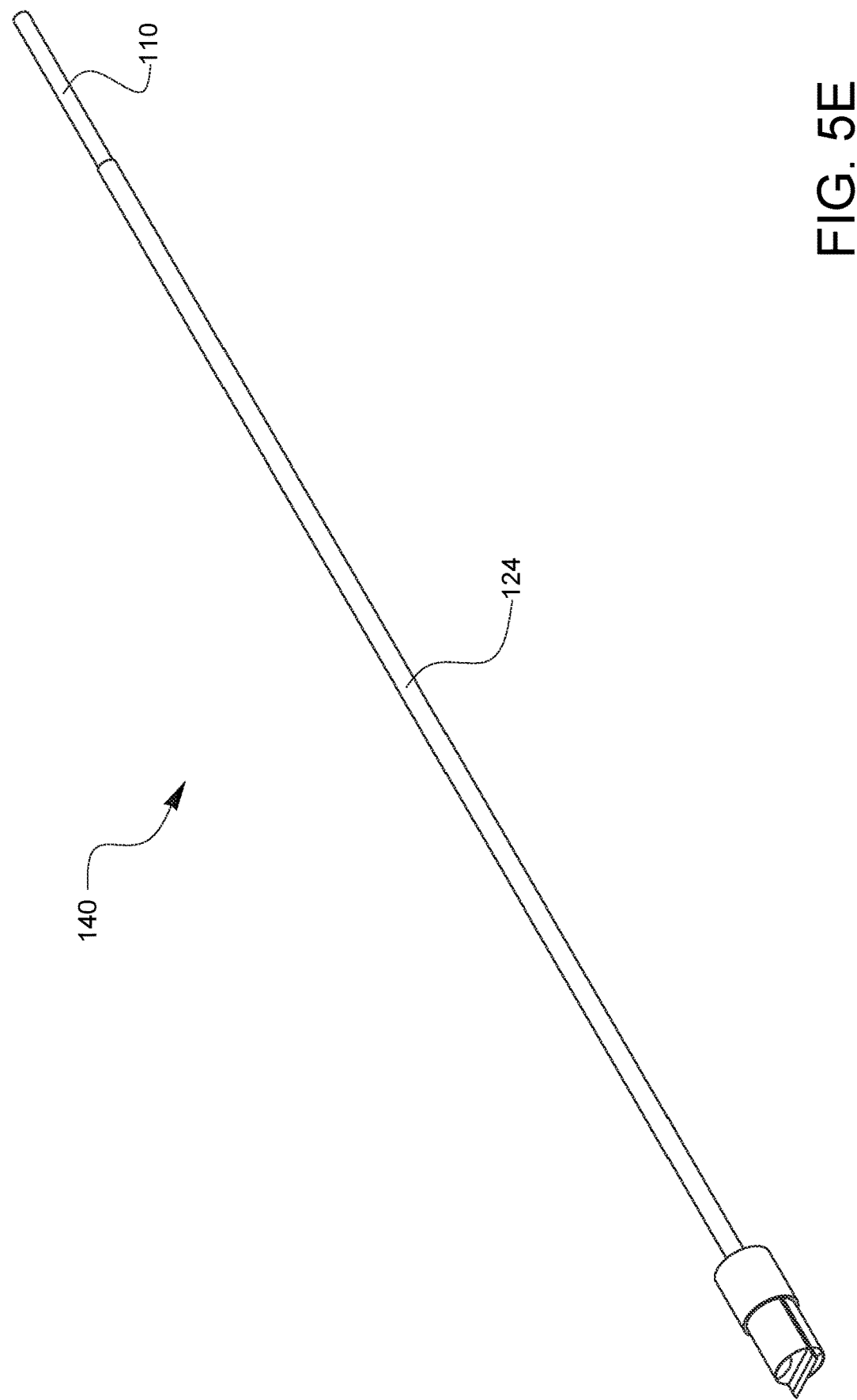
Figure 5F:
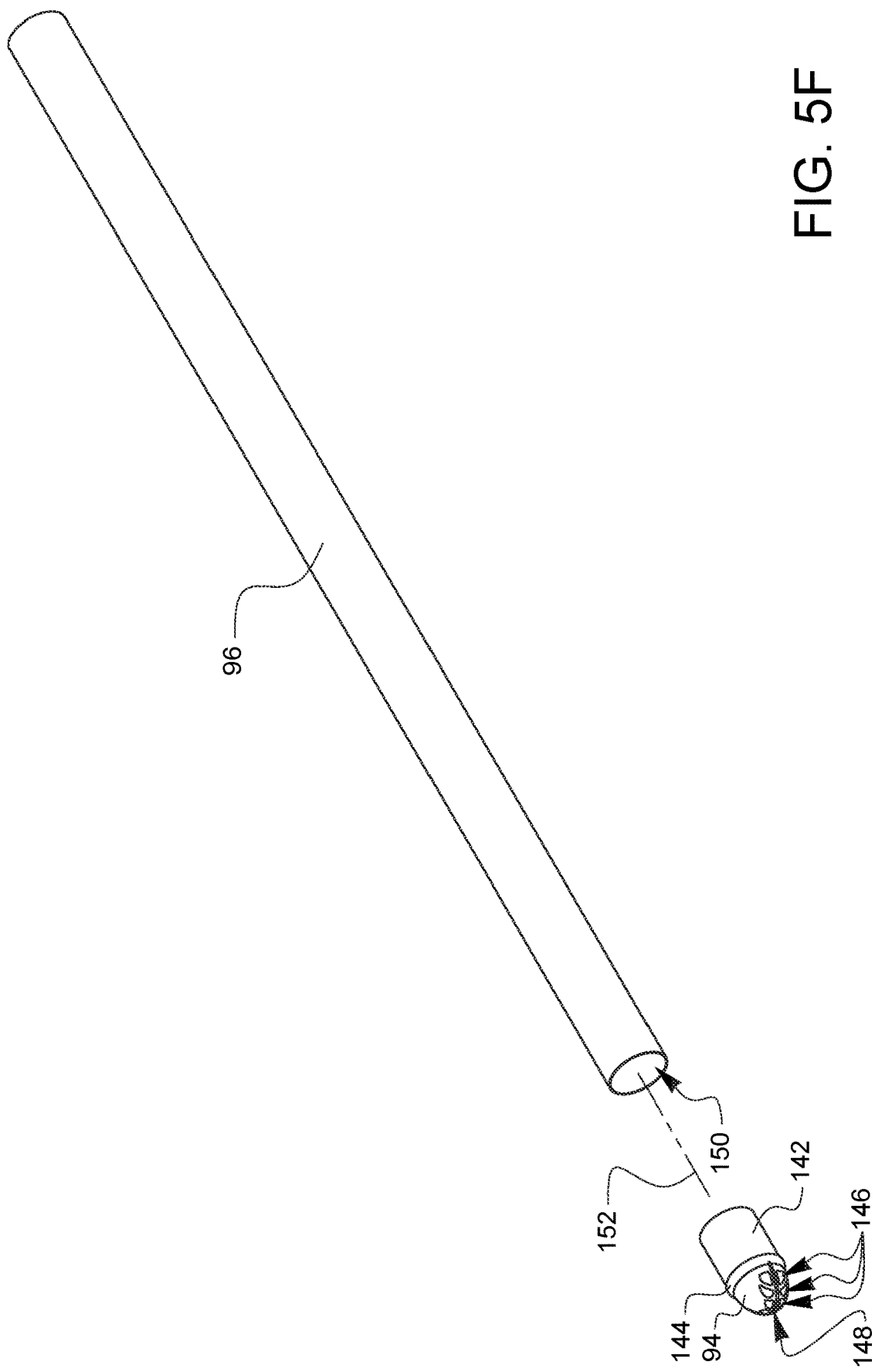
Figure 5H:
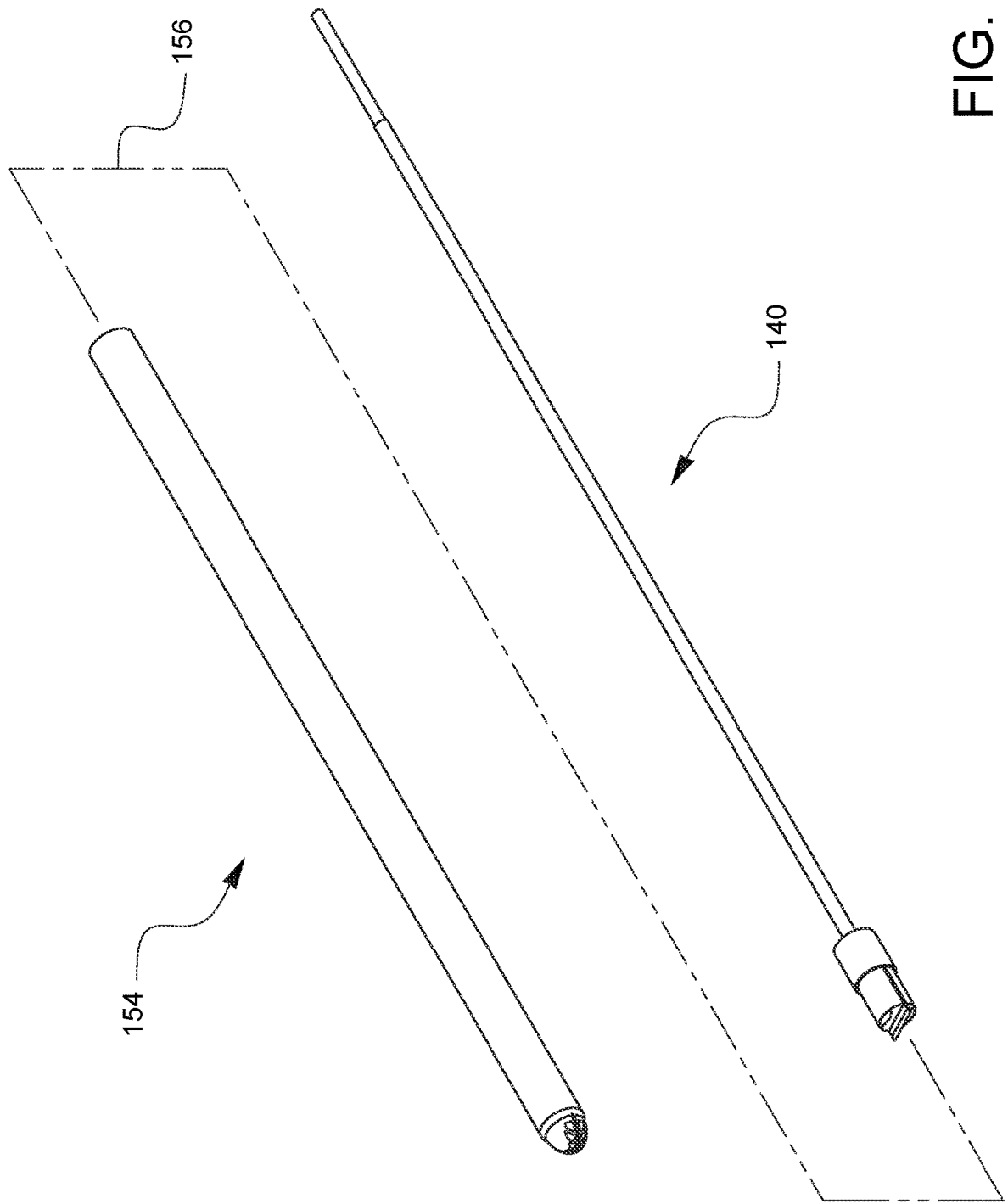
Figure 5J:
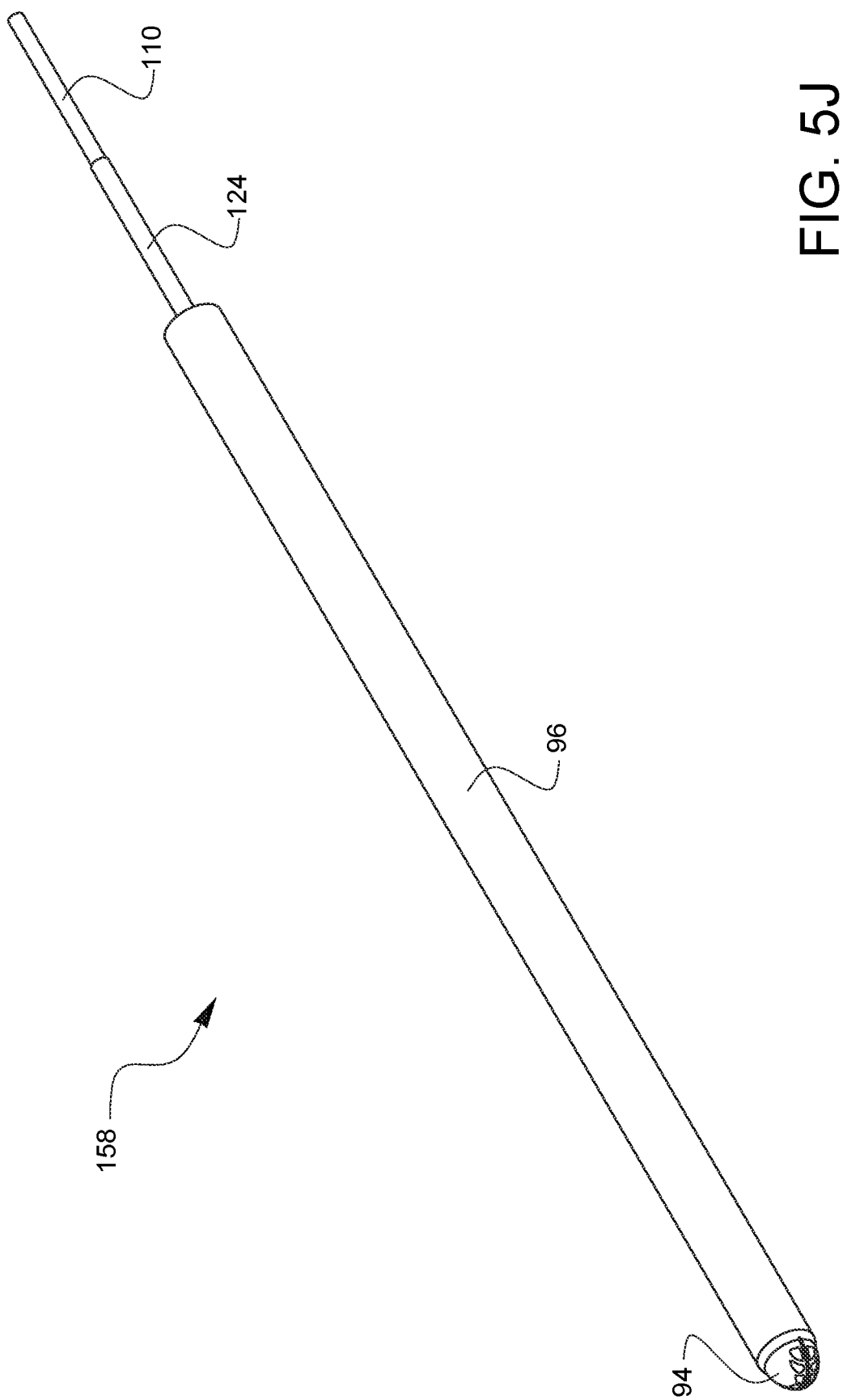
Figure 5L:
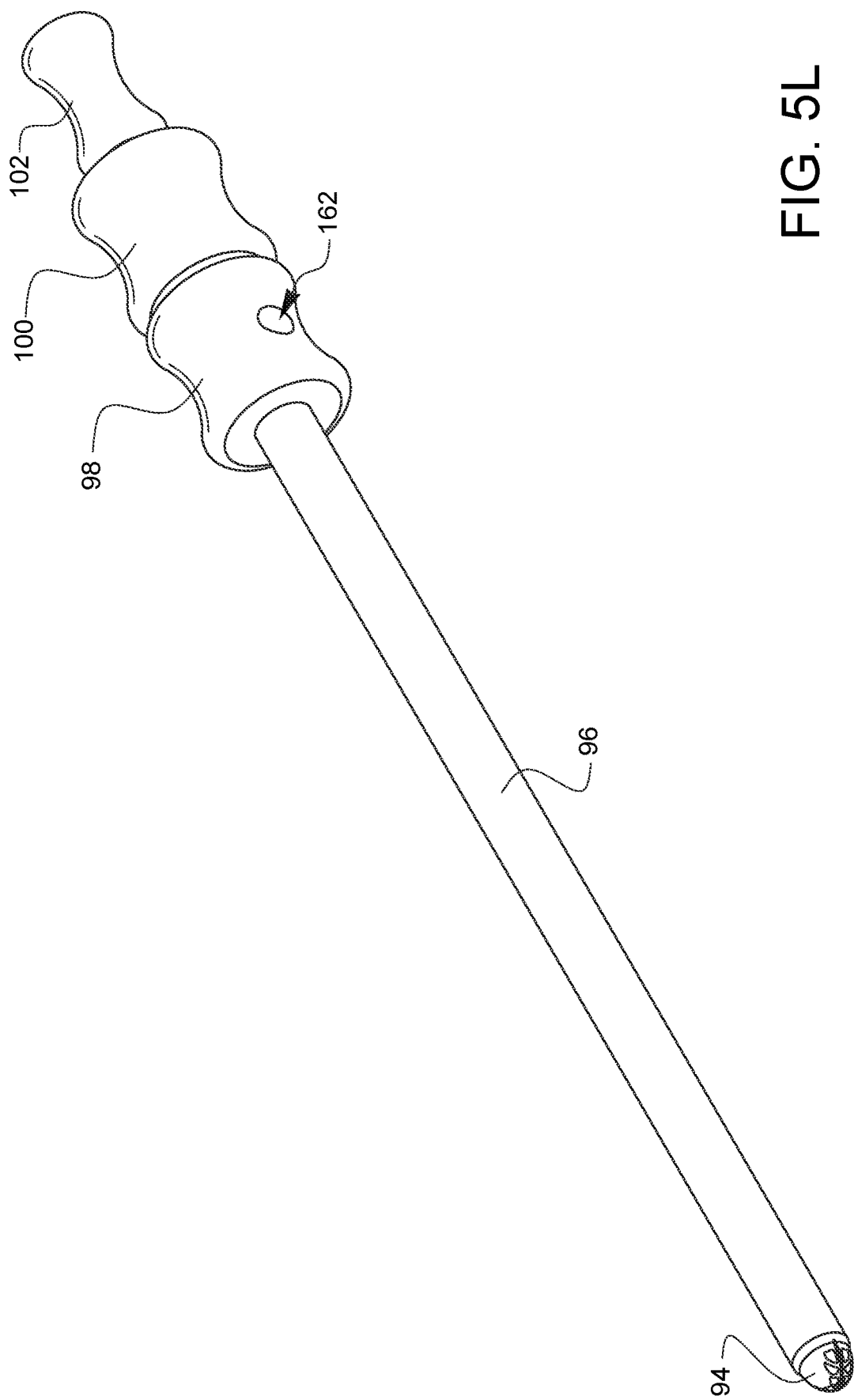
Figure 5M:
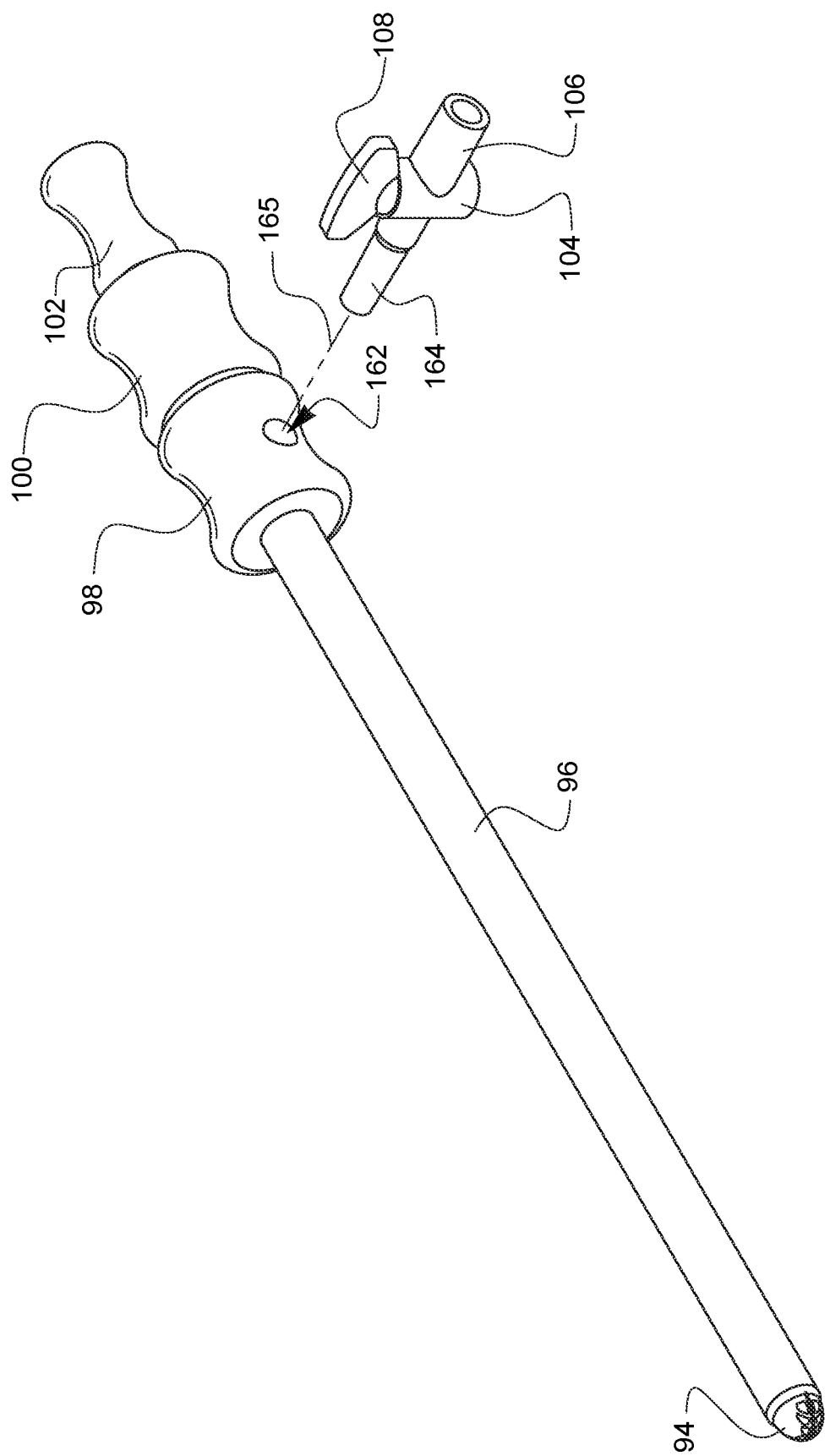
Figure 5N:
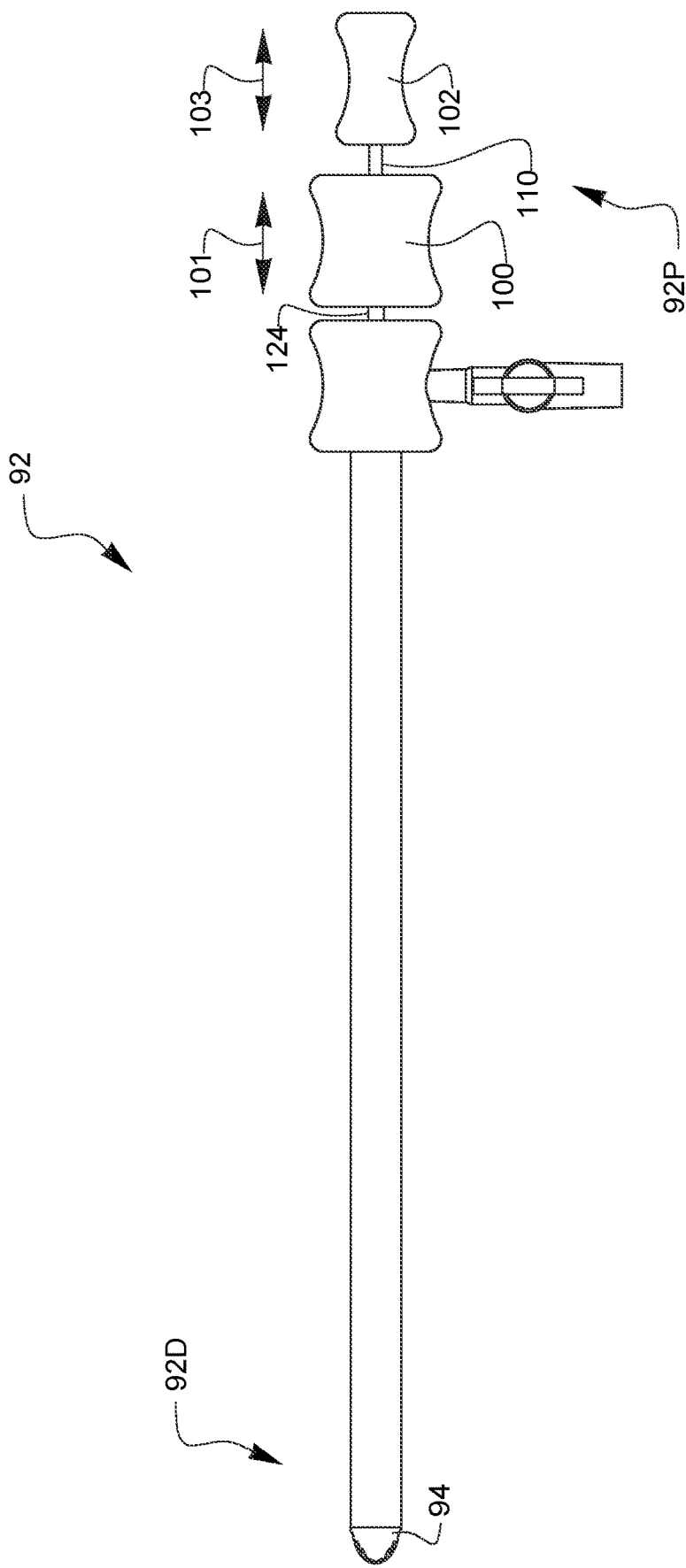

FIG. 5A-5N are a series of exploded views of assembly steps for the obturator portion of the surgical access system of FIG. 4. FIG. 5A illustrates an assembly step of the obturator 92, showing a cutter blade 116 having a cutter blade edge 118 and two holes 117 being inserted along axis 115 into a slot 112 defined by a cutting element drive rod 110. The cutting element drive rod 110 also defines two holes 114 on either side of the slot 112. FIG. 5B illustrates the insertion of two pins 120 through the two holes 114 on the cutting element drive rod 110, through blade holes 117 on the cutter blade 116, and finally through two corresponding holes (not shown in this view) on the opposite side of the cutter drive rod 110. These pins 120 hold the blade on the end of the cutting element drive rod 110. Other embodiments may include a single piece cutting element or similar configurations obvious to those skilled in the art. FIG. 5C illustrates the completed subassembly of a cutting element 122. This retractable element 122 can be actuated independently from other mechanisms within the obturator 92, for example the slidable plunger element, which will be discussed later. While this element 122 is constructed with a mechanical blade as its functional cutting element, other sharpened tools capable of piercing or forming controlled incisions may be useful alternate embodiments of cutting elements, for example, a scalpel, scissors, cauterizing elements, laser elements, and the like. While the cutter blade 116 in this embodiment has a cutter blade edge 118 on the patient-facing or distal side of a rectangular-shaped cutter blade 116, a scalpel may have a triangular-shaped cutter blade having either one side or both sides with a sharpened edge. The retractable cutting element may also be in the form of scissors, wherein two blade members have opposing sharpened edges that slide against each other when actuated or pivoted against one another in contact with tissue to initiate a cutting motion.

FIG. 5D illustrates another assembly step for the obturator portion of the surgical access system of FIG. 4. A vacuum plunger 130 defines a plunger recess 134 having a smaller diameter than the vacuum plunger 130. The vacuum plunger 130 further defines two vacuum ports 136 and a blade slot 138 that communicate throughout the entire length of the vacuum plunger 130. The two vacuum ports 136 are configured to deliver fluid flow from the vacuum inlet 106 of the obturator 92 to the obturator distal tip 94 when the vacuum plunger 130 is pulled back towards a proximal direction, and cut off the fluid flow from the vacuum inlet 106 of the obturator 92 to the obturator distal tip 94 when the vacuum plunger 130 is pushed forward into a more distal direction. The vacuum plunger 130 is further configured to fit tightly within the obturator tube 96 and may have gaskets or other means of sealing or blocking fluid flow between the vacuum plunger 130 and the obturator tube 96. Other embodiments of a vacuum plunger 130 may have different numbers or orientations or shapes of vacuum ports as compared to those illustrated herein. Further, alternate methods of controlling vacuum to the obturator distal tip 94 may be employed and would be known to those skilled in the art. The blade slot 138 is configured to allow the cutter blade edge 118 of the cutting element 122 to pass through the length of the vacuum plunger 130 when the cutting element 122 is inserted into the blade slot 138 of the vacuum plunger 130 along axis 128. The subassembly of FIG. 5D is completed by placing a plunger drive tube 124 over the cutting element 122 along axis 126 and fixedly attaching the plunger drive tube 124 to the vacuum plunger 130. The cutting element 122 is configured to slide back and forth within the plunger drive tube 124. The plunger drive tube 124 or hollow actuator is a slidable plunger element that can be independently actuated from the actuation of the element 122. FIG. 5E illustrates the result of the assembly step for the obturator shown in FIG. 5D. The internal obturator assembly 140 is shown in this view.

FIG. 5F illustrates another assembly step for the obturator portion of the surgical access system of FIG. 4. The obturator distal tip 94 defines a cutting element slot 148, a stop ring 144, several tip ports 146, and a shaft connection recess 142. The cutting element slot 148 is configured to align with the blade slot 138 in the vacuum plunger 130, as described previously, and allow the cutting element 122 to extend through the obturator distal tip 94 when in use. The tip ports 146 are passages for fluid flow to pass therethrough, configured on either side of the element slot 148 such that they do not align with the two vacuum ports 136 on the vacuum plunger 130 when the vacuum plunger 130 is pushed distally. This embodiment illustrates tip ports 146 in two groups of passages, each distinct group located on either side of the blade slot 138. The blade slot 138 may be considered a central passage. In general, these passages are in communication or in contact from the tip of the instrument to the opposite end or port where fluid may be introduced when the fluid flow is turned on or actuated. Conversely, when the fluid flow is turned off, there is an interruption of flow between the tip of the instrument to the opposite end or port where fluid may be introduced. This can be achieved by having hollow cylindrical members throughout, specific ports in various internal components, solid tubes or cylinders with lumens or internal channels, or any combination thereof. There may be alternate embodiments having more than two groups of passages in arrangements known to those skilled in the art. This arrangement effectively cuts off the fluid flow when the vacuum plunger 130 is pushed distally against the inside of the obturator distal tip 94. The obturator tube 96 is a hollow elongated tube or cylinder defining a center 150. Alternate embodiments may not be hollow, but rather solid tubes, and may therefore have lumens or channels along the length of the tube for actuation of various cutting elements, plunger elements, or fluid flow components. The shaft connection recess 142 on the obturator distal tip 94 is configured to be inserted along axis 152 until the stop ring 144 contacts the end of the obturator tube 96. The obturator distal tip 94 is then fixedly attached to the obturator tube 96, completing this assembly step. FIG. 5G illustrates the result of the assembly step for the obturator shown in FIG. 5F. The external obturator assembly 154 is shown in this view. FIG. 5H illustrates another assembly step for the obturator portion of the surgical access system of FIG. 4. The internal obturator assembly 140 of FIG. 5E is inserted into the external obturator assembly 154 of FIG. 5G along axis 156. FIG. 5J illustrates the result of the assembly step for the obturator shown in FIG. 5H. An obturator subassembly 158 is shown in this view, showing the orientation and placement of the obturator distal tip 94, obturator tube 96, plunger drive tube 124, and the cutting element drive rod 110.

FIG. 5K illustrates another assembly step for the obturator portion of the surgical access system of FIG. 4. The obturator subassembly 158 of FIG. 5J is shown. Obturator knob 98 further defines a central hole 164 and a vacuum port 162 configured to communicate fluid flow from the stopcock 104 (not shown here) through to the obturator distal tip 94. The obturator knob 98 is fixedly attached to the obturator tube 96 by sliding the obturator knob 98 over the cutting element drive rod 110 and the plunger drive tube 124 and onto the end of the obturator tube 96. Plunger knob 100 defines a central hole 166 and is fixedly attached to the plunger drive tube 124 by inserting the plunger drive tube 124 into the central hole 166 of the plunger knob 100 along axis 160. It should be noted that the plunger drive tube 124 and the attached plunger knob 100 move independently from the previously installed obturator knob 98 as well as independently from the cutting element drive rod 110. The cutter knob 102 also defines a central hole. Finally, the cutting element drive rod 110 is inserted into the central hole 168 on the cutter knob 102 along axis 160 and fixedly attached thereto. In this embodiment, the obturator knob 98 does not move once assembled in the obturator. The plunger knob 100 moves the plunger drive tube 124 and therefore the vacuum plunger 130 distally and proximally independent from the obturator knob 98 and the cutter knob 102. This plunger knob may also be considered an actuator or a plunger actuator as this feature is used to actuate or influence the movement of the vacuum plunger 130 and therefore actuate the fluid flow through the obturator 92 on or off as appropriate. Also, the cutter knob 102 moves the cutting element drive rod 110 and hence the cutter blade 116 distally and proximally independent from the obturator knob 98 and the plunger knob 100. This cutter knob 102 may also be considered an actuator or a cutting actuator as this feature is used to actuate or influence the movement of the cutting element 122. The cutting element drive rod 110 may also be considered an actuator rod, or an actuation drive rod as this rod or wire is used to actuate or move the cutter blade 116 in and out of the cutting element slot 148 in the obturator distal tip 94. FIG. 5L illustrates the result of the assembly step for the obturator shown in FIG. 5K, showing the assembled orientation and positions of the obturator distal tip 94, obturator tube 96, obturator knob 98, plunger knob 100, and cutter knob 102.

FIG. 5M illustrates the final assembly step for the obturator portion of the surgical access system of FIG. 4. The vacuum port 162 defined by the obturator knob 98 is a fluid passage configured to accept the stopcock 104 by inserting the central hole 164 defined by the stopcock 104 into the vacuum port 162 along axis 165. The vacuum port 162 is a passage that allows for fluid flow from outside of the surgical access system to the inside of the obturator tube 96 of the obturator 92. This assembly step results in the obturator 92 of FIG. 4.

FIG. 5N is a side view of the obturator portion of the surgical access system of FIG. 4. The side view shows the assembled obturator 92 with additional details regarding the articulation of the plunger knob 100 and the cutter knob 102. Arrow 101 indicates the direction of articulation of the plunger knob 100. When plunger knob 100 is moved toward the distal end 92D of the obturator 92, the plunger drive tube 124 coupled to plunger knob 100 also moves distally and independently from the inserted cutter drive rod 110, and the fluid flow through the obturator 92 is cut off, as previously described. Conversely, when the plunger knob 100 is moved toward the proximal end 92P of the obturator 92, plunger knob 100 also moves proximally along with the coupled vacuum plunger 130, and the fluid flow through the obturator 92 is turned on. Arrow 103 indicates the direction of articulation of the cutter knob 102. When cutter knob 102 is moved toward the distal end 92D of the obturator 92, cutter drive rod 110 also moves distally, independently within the plunger drive tube 124, and cutter blade 116 is actuated or advanced out of the obturator tip 94, as previously described. Conversely, when cutter knob 102 is moved toward the proximal end 92P of the obturator 92, cutter drive rod 110 also moves proximally, independently within the plunger drive tube 124, and cutter blade 116 is retracted into the obturator tip 94.

Figure 6A:
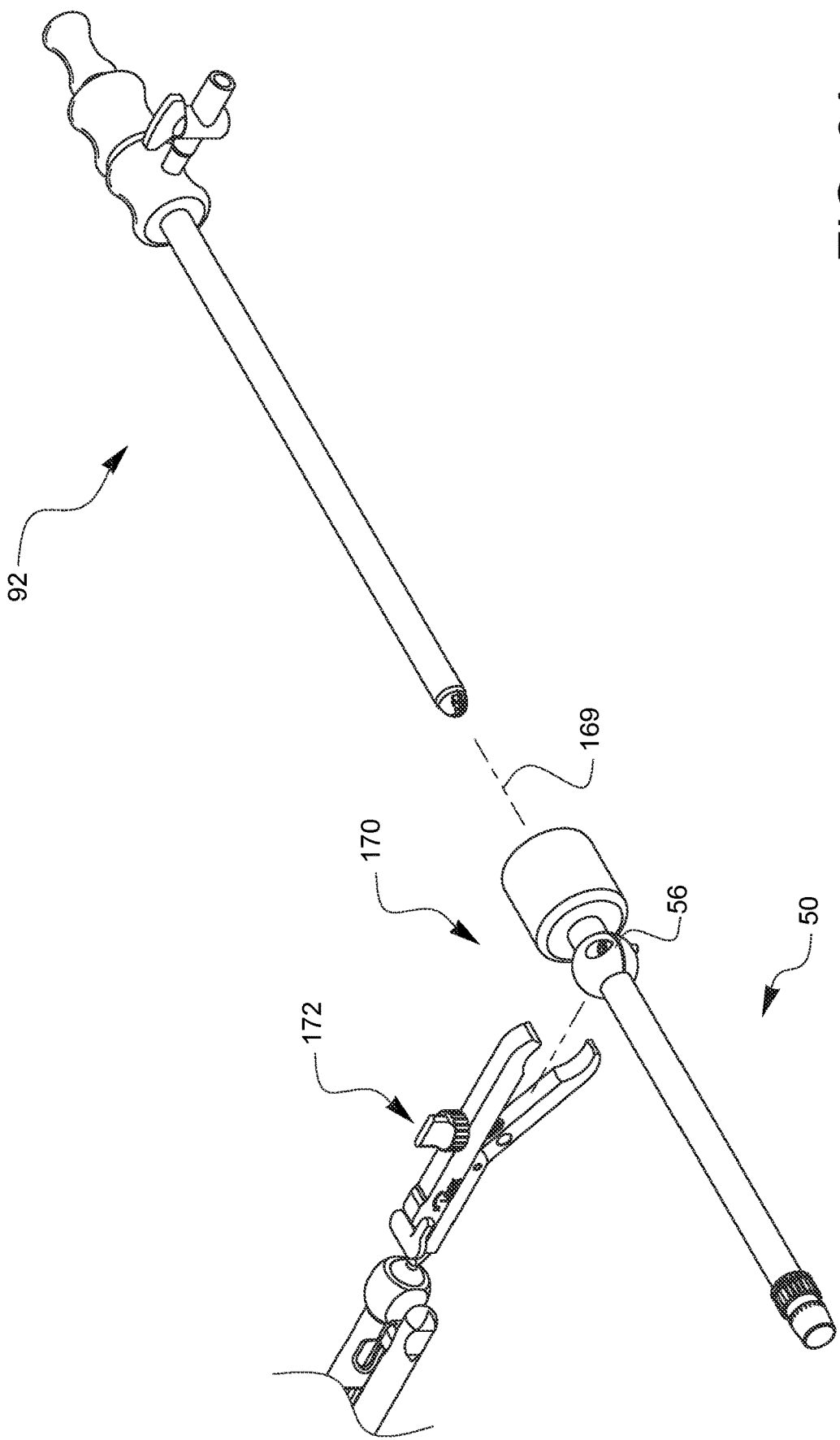
FIG. 6A is an exploded view illustrating an assembly step for a surgical access system.
Figure 6B:
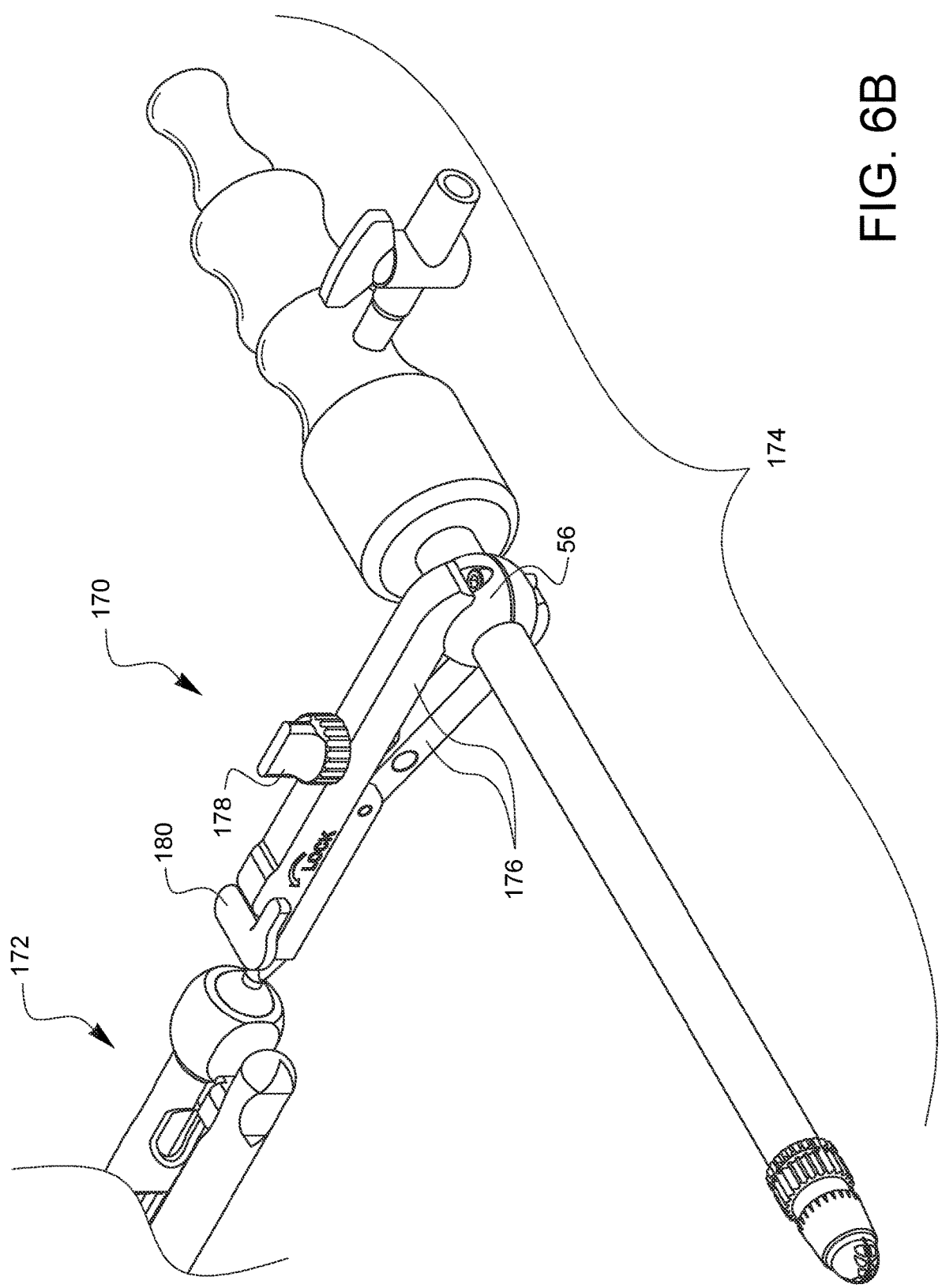
FIG. 6B is a perspective view of the surgical access system of FIG. 5A.

FIG. 6A is an exploded view illustrating an assembly step for a surgical access system. FIG. 6A shows an optional surgical instrument holder 172 terminating with a clamp adapter 170 attached to its end. The clamping adapter 170, shown open, is placed over the universal ball joint 56 of the cannula 50 of FIG. 2, the jaws 176 are closed and tightened by tightening the adjustment screw 178. The obturator 92 of FIG. 4 is inserted into the center of the cannula 50 along axis 169. FIG. 6B is a perspective view of the surgical access system of FIG. 6A.

A surgical access system 174 is illustrated which can be used to provide access to a patient's right atrium for the purpose of performing a minimally invasive tricuspid valve repair as previously described. Similar embodiments of the surgical access system 174 may also be useful in other procedures where minimally invasive access to a surgical site is advantageous. The surgical access system has the cannula 50, the obturator 92, and the universal ball joint 56. The universal ball joint is held in a clamp adapter 170 having an adjustment screw 178 and a lever lock 180. The clamp adapter 170 is attached to a surgical instrument holder 172 which holds the surgical access system 174 in a potential initial position for use in a minimally invasive surgical procedure. The clamp adapter 170 has jaws 176 which hold the universal ball joint 56 that is slidably attached to the cannula tube, as previously described. Alternate embodiments of a clamping adapter or alternate clamping elements would be known to those skilled in the art. The universal ball joint 56 in combination with the clamp adapter 170 and the surgical instrument holder 172 provide multiple degrees of freedom of movement and the ability to position the surgical access system in any number of positions advantageous for targeted access to a minimally invasive surgical site. Suitable surgical equipment holders, such as, but not limited to, the miniARM™ INSTRUMENT HOLDER from LSI Solutions, Inc. (Victor, NY, www.lsisolutions.com) are intended for use in such surgical procedures.

An advantageous feature of the articulation interface in the embodiments described herein is that the universal ball joint 56 can first be set along the length of the cannula tube 54 depending on anatomical variations as appropriate. This provides articulation along the axis of the cannula tube 54, providing articulation in one plane. Having a substantially spherical universal ball joint 56 held within a clamping element or clamp adapter 170 as shown provides adjustment in the remaining two dimensions. This arrangement of the universal ball joint 56 and the clamp adapter 170 provides articulation in all planes and is thus repositionable by a surgeon to flexibly provide access to a minimally invasive surgical site. With the clamp adapter 170 attached to a surgical instrument holder 172 as shown in FIGS. 6A and 6B, even further adjustability and repositionability may be attained by the operator or surgeon. Alternatively, a universal joint may be used in a surgical access system such as the one described herein. A universal joint is a coupling or joint that connects more than one segment, tube, rod or limb on a general apparatus. The segment axes are inclined to each other and may or may not transmit rotary motion. The coupling includes a pair of hinges in proximity to one another, connected by a cross-shaped shaft. A universal joint configured in such an arrangement allows for rotational motion of the rods or segments while the rods or segments coupled by the joint are not oriented in a straight line.

Figure 7A:
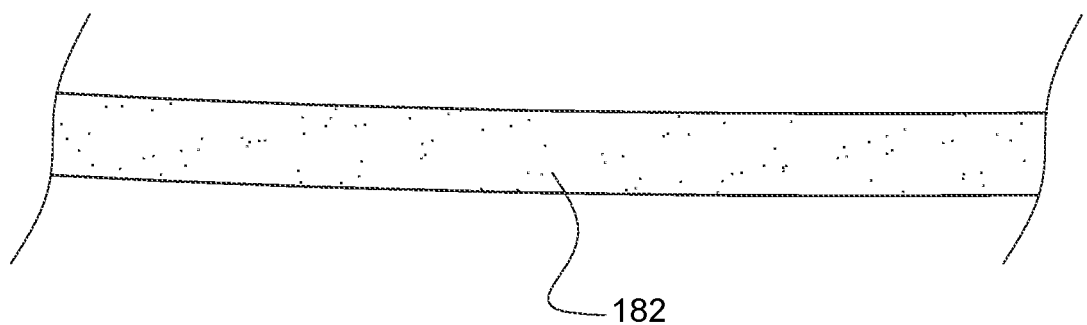
FIGS. 7A-7E are several side-views of surgical steps illustrating the use of the surgical access system of FIG. 5A.

FIGS. 7A-7E are several side-views of surgical steps illustrating one use of the surgical access system of FIG. 6B. FIG. 7A illustrates the wall of the right atrium or the right atrial wall 182, which is the target surgical site for a surgical access system such as the one described herein. In preparation for use of the surgical access system, the location of the universal ball joint 56 along the length of the cannula tube 54 is set. An appropriate right anterior access site is selected, and an incision is made within the 2nd intercostal space, at the right lateral border of the chest wall. The subcutaneous tissue and along with major muscle fibers and intercostal muscle fibers are split and divided, using blunt dissection whenever possible. A suitable access port is installed, optionally with the use of a retractor. Also optional is the use of an appropriate suture management apparatus. Further dissection, movement, or removal of fat or other tissue is performed as needed. During the subsequent steps of the surgical procedure outlined herein, additional visualization methods may be used to aid placement of the surgical access system 174.

Figure 7B:
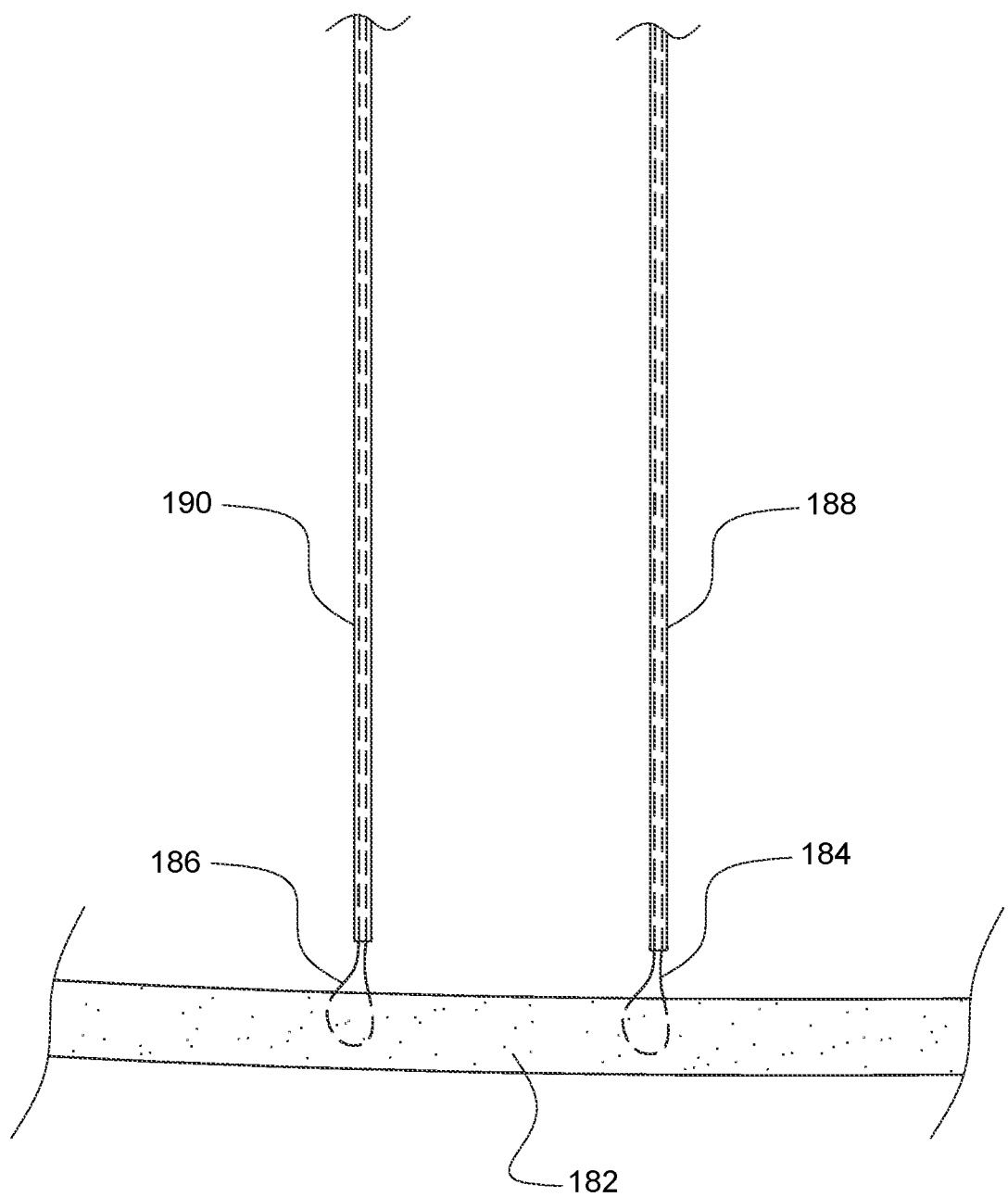

FIG. 7B is a side-view of a surgical step illustrating the use of the surgical access system of FIG. 6B. FIG. 7B illustrates two concentric pursestring sutures 184, 186 about the right atrial wall 182 incision site so that one end of each pursestring suture enters and exits the right atrial wall 182. This can be accomplished using a suitable surgical suturing device such as, but not limited to, the PRESTIGE™ device from LSI Solutions, Inc. (Victor, NY, www.lsisolutions.com). Once the pursestring sutures 184, 186 are completed, they are both snared, using a device such as, but not limited to, a MINI-RUMEL® device from LSI Solutions, Inc. (Victor, NY, www.lsisolutions.com) for each of the pursestring sutures 184, 186. FIG. 7B illustrates both pursestring sutures 184, 186 snared and encapsulated within their respective suture tubes 188, 190. Such a device is one method of employing a suture snare, but other means of snaring, organizing and encapsulating sutures during a minimally invasive surgical procedure may be well known to those skilled in the art. Examples include, a simple snare in tube arrangement where the suture or snare may be held in position with common clamping methods such as butterfly clamps and the like, or where a suture locking apparatus may be used to lock and unlock the position of a suture within a tube releasably and repeatedly. The suture tubes 188, 190 are attached to the longitudinal grooves 84 located on the distal tip 52 of the cannula 50. The longitudinal grooves 84 or channels are configured to releasably hold sutures or suture tubes such that they are held close to the cannula during use. Prior to subsequent surgical steps illustrated herein, the suture tubes 188, 190 are further secured to the distal tip 52 of the cannula 50 using a cinch suture 192 along the cinch suture channel 86 of the cannula tip 52 as shown in FIG. 7C.

Figure 7C:
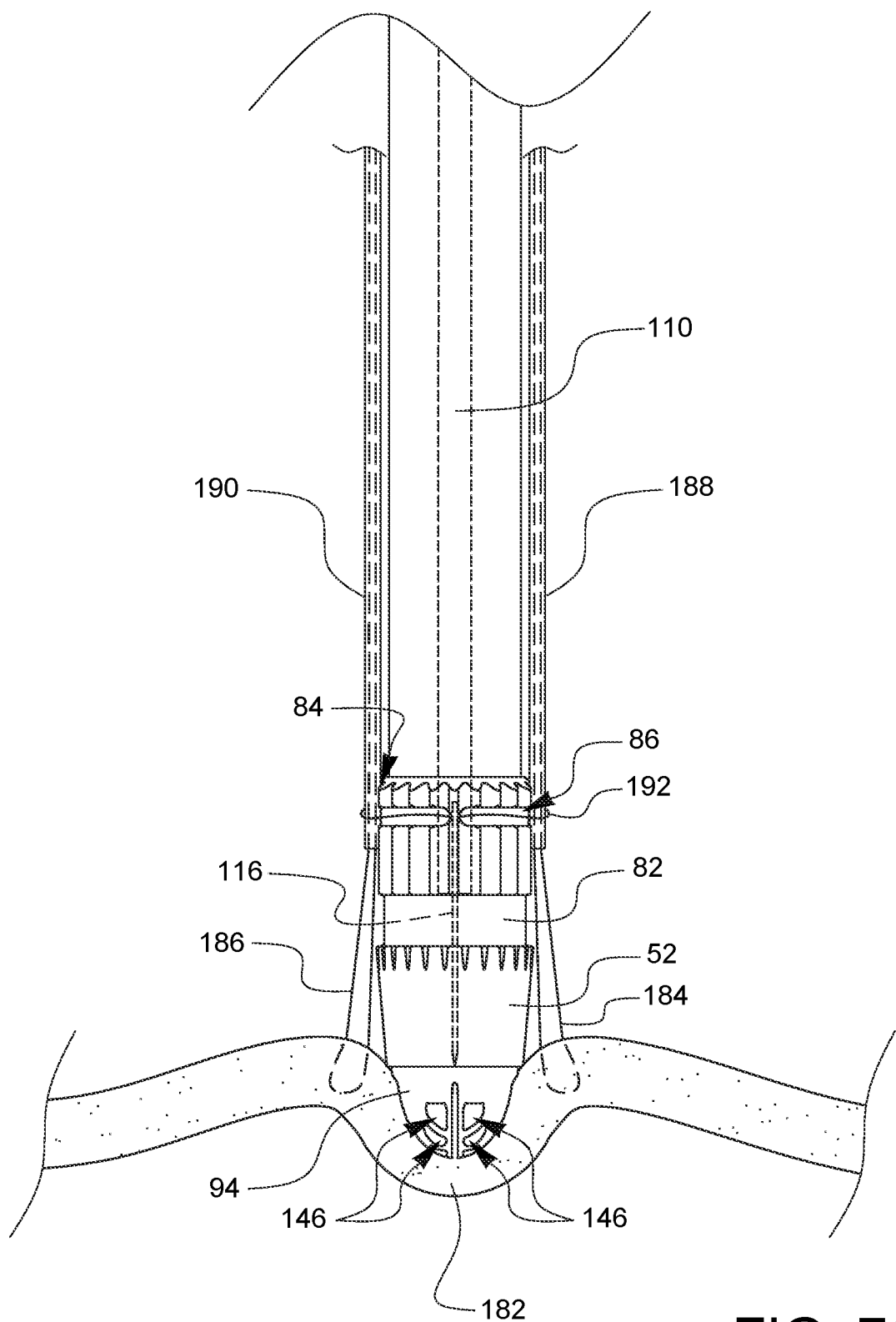

FIG. 7C is a side-view of a surgical step illustrating the use of the surgical access system of FIG. 6B. The surgical step illustrates the next steps in an exemplary surgical sequence utilizing the surgical access system 174 described herein. FIG. 7C shows the distal end 174D of the surgical access system 174 introduced into the surgical site and moved into position with the obturator distal tip 94 in direct contact with the right atrial wall 182. The universal ball joint 56 has been translated to the appropriate position on the cannula tube 54 to account for the distance from the chest wall of the patient and the right atrial wall 182. The cinch suture 192 is shown threaded over the suture tubes 188, 190, through the cinch suture channel 86 and into one or more bridge orifice 89 located under one or more bridges 88 located on the cannula tip 52. The cinch suture 192 further secures the suture tubes 188, 190 around the circumference of the cannula 50 of the surgical access system 174. The suture tubes 188, 190 are also held into their respective longitudinal grooves 84 with the cinch suture 192 providing added security. It should be noted that pursestring suture 184, 186 movement is not restricted within the suture tubes 188, 190 when secured by the cinch suture 192. The cinch suture 192 may be fastened using a knot or mechanical fastener, but is not shown in this view. The suction feature of the obturator tip 94 should be activated as described previously, by opening the stopcock valve on the obturator knob, and actuating the plunger knob and therefore the plunger drive tube and the vacuum plunger. The activation of the vacuum flow brings the tissue of the right atrial wall 182 under additional tension against the obturator distal tip 94 by applying suction through the obturator distal tip 94 via the tip ports 146 which are grouped on either side of the blade slot 138. The blade slot 138 is an elongated passage through which a blade element or cutting element can pass through, and is separate from the passages in the obturator distal tip 94 that permit fluid flow through the obturator distal tip 94.

Figure 7D:
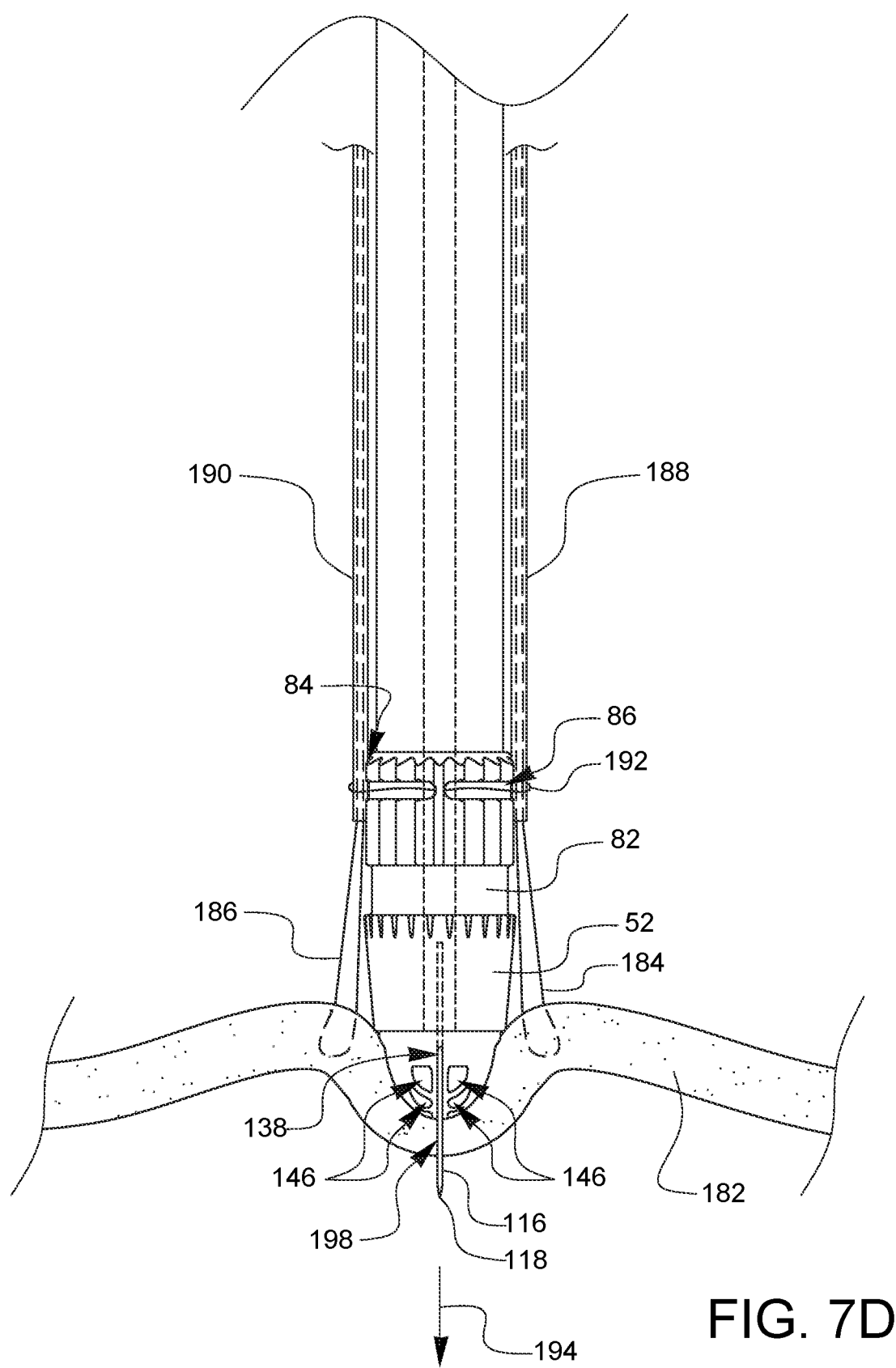

FIG. 7D is a side-view of a surgical step illustrating the use of the surgical access system of FIG. 6B. FIG. 7D shows the actuation of the retractable blade of the surgical access system 174. While the obturator distal tip 94 is in close contact with the right atrial wall 182, the cutter knob 102 is actuated by the user at the proximal end of the obturator 92 by pushing the cutter knob 102 in direction 194, towards the right atrial wall 182. Actuating the cutter knob 102 in turn pushes the cutting element drive rod 110 and likewise the cutter blade edge 118 of the cutter blade 116 in direction 194, incising the tissue of the right atrial wall 182. This leaves an incision 198 in the right atrial wall 182 tissue.

Figure 7E:
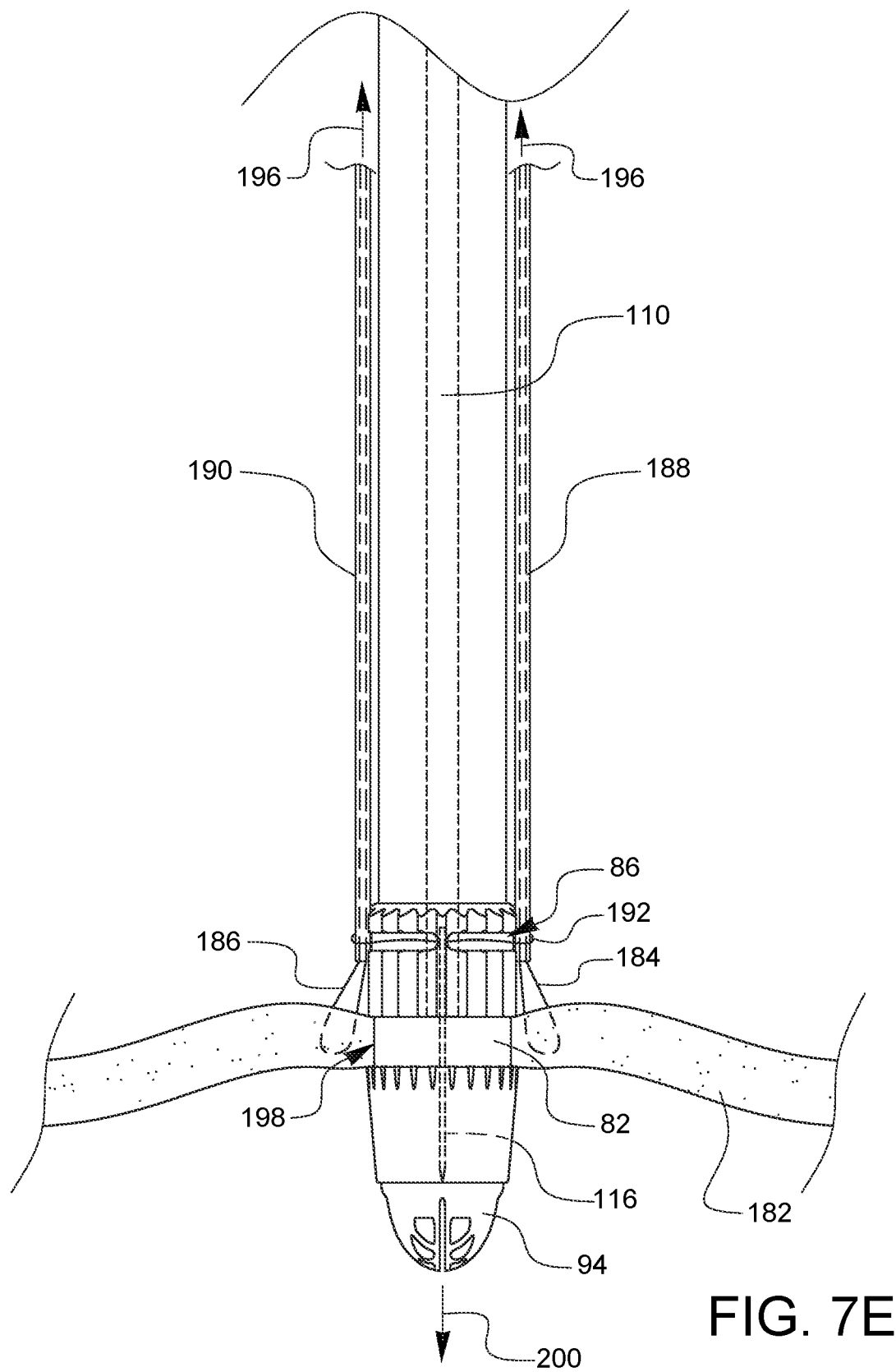

FIG. 7E is a side-view of a surgical step illustrating the use of the surgical access system of FIG. 6B. After the incision 198 is made in the right atrial wall 182, the cutter blade 116 is quickly retracted and the cannula tip 52 is advanced into the incised right atrial wall 182 at the site of the incision 198. The cannula tip 52 is advanced until the right atrial wall 182 is placed within the circumferential pursestring suture channel 82 of the cannula tip 52 at the point of incision 198. The pursestring sutures 184, 186 are snugged using suture locks or other apparatus such as MINI-RUMEL®. Appropriate positioning of the cannula 50 location is can again be confirmed by adjustment of the universal ball joint 56 within the clamp adapter 170 and by repositioning the surgical instrument holder 172. Suction is also turned off and discontinued at this point. The obturator 92 portion of the surgical access system 174 is removed from the incision 198 and from the minimally invasive surgical site, leaving the cannula 50 in place for any additional surgical procedures to be performed.

FIGS. 8A-8F are front, left side, right side, rear, top, and bottom elevational views, respectively, of the distal tip of the cannula of FIG. 3. These views illustrate in greater detail and from various points of view the features of the cannula tip 52 including the circumferential pursestring suture channel 82, the longitudinal grooves 84, the cinch suture channel 86, the cannula tip opening 90, and several bridges 88. As shown previously, each bridge 88 defines a bridge orifice 89, which accommodates the cinch suture. The cinch suture can go over or under the bridge 88 and may not necessarily be threaded through the bridge orifice 89. Alternate embodiments of cannula tips may not have bridges or orifices. Alternate embodiments of cannula tips may have a differently configured or angled tip and may have differing numbers of grooves or of orifices for retaining suture, thread, wire or tissue.

Figure 9A:
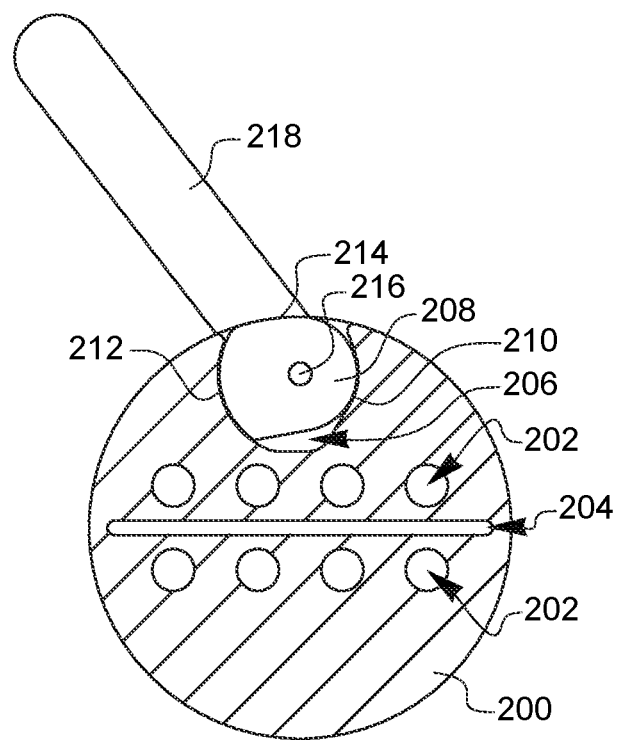
FIGS. 9A and 9B are front views of an alternate embodiment of an obturator for a surgical access system illustrating a rotating ramp feature.
Figure 9B:
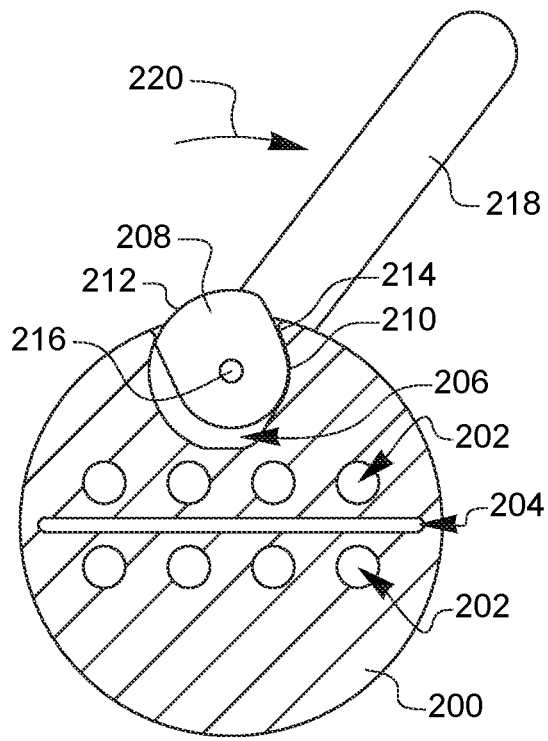

FIGS. 9A and 9B are front-views of an alternate embodiment of an obturator for a surgical access system illustrating a rotating ramp feature. FIG. 9A shows a front view of a distal tip of the obturator in a retracted position. An obturator distal tip 200 as previously described defining several tip ports 202 and a cutting element slot 204 also defines a ramp recess 206 located on the outer circumference of the obturator distal tip 200. The ramp recess 206 is sized and configured to accommodate the rotational movement of a rotation ramp 208, which is shown here as a partial circular shaped element. The rotation ramp defines an external profile having a base surface 210 and a ramp surface 212, and a side profile surface 214. The base surface 210 is substantially circular as observed from the front-end view as shown in FIG. 9A, while the ramp surface 212 extends circumferentially beyond the substantially circular profile defined by the base surface 210 when rotated. The side profile surface 214 defines an arc that follows the outer circumferential profile of the obturator distal tip 200 when the rotation ramp 208 is in the retracted position. The rotation ramp 208 rotates about a pivot point 216. This rotation is controlled by an actuator 218, which in this embodiment is depicted as a lever, placed at a location proximal to the obturator distal tip 200, such as near the obturator knob 98 described previously, for example.

FIG. 9B shows a front view of a distal tip of the obturator in an extended position. The actuator 218 has been moved in a direction 220 that in turn has rotated the rotation ramp 208 about the pivot point 216 such that the side profile surface 214 has been moved into the ramp recess 206 and the ramp surface 212 is now located on the outer circumference of the obturator distal tip 200 which increases the effective circumference of the obturator distal tip 200 temporarily while the rotation ramp 208 is in the extended position. It should be noted that shapes other than the one shown may be utilized in a rotation ramp 208 for the purpose of temporarily increasing the effective circumference of the obturator distal tip 200. In the event that additional circumference or girth is required to assist in advancing the cannula and obturator of the surgical access system into the incised atrial wall, the rotation ramp 208 has a shape that when rotated provides a temporary increase in the effective circumference of the obturator tip 200. The rotation ramp 208 can be actuated, extended, or retracted by an actuator 218 such as the illustrated lever, or alternatively a button, a knob, or other means known to those skilled in the art. The actuator may alternatively be in other places on the obturator. The rotation ramp 208 is further configured within the obturator distal tip 200 in such a fashion that when the obturator is fully inserted into the cannula in the described surgical access system, the rotation ramp 208 extends beyond the cannula tip such that the rotation ramp 208 can be extended past the circumference defined by the surgical access system. In an actuated or extended position as shown in FIG. 9B, the rotation ramp 208 expands or pulls tissue in an outward direction such that it assists in getting tissue over the cannula tip and into cannula tip circumferential pursestring suture channel.

Various advantages of a surgical access system used, for example, for repair of tricuspid regurgitation, and methods thereof have been discussed above. Embodiments discussed herein have been described by way of example in this specification. It will be apparent to those skilled in the art that the forgoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:

1. A surgical access system, comprising:
    a cannula comprising:
        a distal tip having:
            one or more longitudinal channels distributed around a circumference of the distal tip;
            one or more circumferential channels around the distal tip; and
            one or more bridges distributed circumferentially along the one or more circumferential channels; and
    an obturator coaxially insertable within the cannula comprising:
        a distal tip; and
        a retractable cutting element having an actuator; and
    an articulation interface.

2. The surgical access system of claim 1, wherein the cannula and the articulation interface are continuous.

3. The surgical access system of claim 1, wherein the obturator further comprises an elongated tube.

4. The surgical access system of claim 3, wherein the obturator further comprises an obturator knob having a passage in communication with an inside of the elongated tube of the obturator.

5. The surgical access system of claim 3, wherein the distal tip of the obturator further comprises one or more passages in communication with an inside of the elongated tube of the obturator.

6. The surgical access system of claim 5, wherein the distal tip of the obturator further comprises two groups of one or more passages, the groups of one or more passages separated by a central passage.

7. The surgical access system of claim 3, wherein the obturator further comprises a slidable plunger element configured to control fluid flow inside the elongated tube of the obturator.

8. The surgical access system of claim 7, wherein the obturator further comprises a hollow actuator coupled to the slidable plunger element.

9. The surgical access system of claim 8, wherein the obturator further comprises an actuator rod coupled to the retractable cutting element.

10. The surgical access system of claim 9, wherein the actuator rod coupled to the retractable cutting element is slidably engaged inside the hollow actuator coupled to the slidable plunger element.

11. The surgical access system of claim 1, wherein the retractable cutting element is selected from the group consisting of a blade, a scalpel, and scissors.

12. The surgical access system of claim 1, wherein the articulation interface is substantially spherical.

13. The surgical access system of claim 1, wherein the articulation interface is repositionable along the cannula.

14. The surgical access system of claim 1, wherein the articulation interface is continuous with the cannula.

15. The surgical access system of claim 1, wherein the articulation interface comprises a universal joint.

16. The surgical access system of claim 1, further comprising a rotation ramp.

17. A surgical access system, comprising:
    a cannula comprising:
        a distal tip having:
            one or more longitudinal channels distributed around a circumference of the distal tip; and
            one or more circumferential channels around the distal tip;
    an obturator coaxially insertable within the cannula comprising:
        a distal tip;
        a retractable cutting element having an actuator;
        an elongated tube;
        a slidable plunger element configured to control fluid flow inside the elongated tube of the obturator;
        a hollow actuator coupled to the slidable plunger element; and
        an actuator rod coupled to the retractable cutting element, wherein the actuator rod coupled to the retractable cutting element is slidably engaged inside the hollow actuator coupled to the slidable plunger element; and
    an articulation interface.

18. The surgical access system of claim 17, wherein the articulation interface is substantially spherical.

19. The surgical access system of claim 17, wherein the articulation interface is repositionable along the cannula.

20. The surgical access system of claim 1, wherein the articulation interface is continuous with the cannula.

21. The surgical system of claim 17, wherein the articulation interface comprises a universal joint.

22. A surgical access system, comprising:
    a cannula comprising:
        a distal tip having:
            one or more longitudinal channels distributed around a circumference of the distal tip; and
            one or more circumferential channels around the distal tip;
    an obturator coaxially insertable within the cannula comprising:
        a distal tip; and
        a retractable cutting element having an actuator; and
        a rotation ramp; and
    an articulation interface.

* * * * *